United States Patent
Filipovska et al.

(10) Patent No.: US 9,580,714 B2
(45) Date of Patent: Feb. 28, 2017

(54) PEPTIDES FOR THE SPECIFIC BINDING OF RNA TARGETS

(75) Inventors: Aleksandra Filipovska, Western Australia (AU); Oliver Rackham, Western Australia (AU)

(73) Assignee: The University of Western Australia, Western Australia (AU)

( * ) Notice: Subject to any disclaimer, the term of this patent is extended or adjusted under 35 U.S.C. 154(b) by 0 days.

(21) Appl. No.: 13/989,676

(22) PCT Filed: Nov. 24, 2011

(86) PCT No.: PCT/AU2011/001519
§ 371 (c)(1),
(2), (4) Date: May 24, 2013

(87) PCT Pub. No.: WO2012/068627
PCT Pub. Date: May 31, 2012

(65) Prior Publication Data
US 2013/0323813 A1 Dec. 5, 2013

(30) Foreign Application Priority Data
Nov. 24, 2010 (AU) .................. 2010905192

(51) Int. Cl.
*A61K 38/00* (2006.01)
*C12N 15/64* (2006.01)
*C07K 14/435* (2006.01)
*C07K 14/47* (2006.01)

(52) U.S. Cl.
CPC ........ *C12N 15/64* (2013.01); *C07K 14/43545* (2013.01); *C07K 14/43581* (2013.01); *C07K 14/47* (2013.01); *A61K 38/00* (2013.01); *C07K 2319/02* (2013.01); *C07K 2319/09* (2013.01); *C07K 2319/20* (2013.01); *C07K 2319/60* (2013.01); *C07K 2319/85* (2013.01)

(58) Field of Classification Search
None
See application file for complete search history.

(56) References Cited

U.S. PATENT DOCUMENTS

2013/0129701 A1* 5/2013 Wang et al. ................. 424/94.3

OTHER PUBLICATIONS

Sanjanwala and Ganesan, PNAS: vol. 86, pp. 4421-4424, Jun. 1989.*
International Search Report for PCT/AU2011/001519, Completed by the Australian Patent Office on Dec. 5, 2011, 3 Pages.
Tuschl et al. Genes Dev. 1999, vol. 13, p. 3191-3197, "Targeted mRNA degradation by double-stranded RNA in vitro."
Schwarz et al. Cell Oct. 17, 2003, vol. 115, p. 199-208, "Asymmetry in the Assembly of the RNAi Enzyme Complex."
Judge et al. Human Gene Therapy Feb. 2008, vol. 19, p. 111-124, "Overcoming the Innate Immune Response to Small Interfering RNA."
Spassov et al. IUBMB Life Jul. 2003, vol. 55, No. 7, p. 359-366, "The PUF Family of RNA-binding Proteins: Does Evolutionarily Conserved Structure Equal Conserved Function?"
Edwards et al. Cell Apr. 20, 2001, vol. 105, p. 281-289, "Structure of Pumilio Reveals Similarity between RNA and Peptide Binding Motifs."
Wang et al. Cell Aug. 23, 2002, vol. 110, p. 501-512, "Modular Recognition of RNA by a Human Pumilio-Homology Domain."
Cheong et al. PNAS Sep. 12, 2006, vol. 103, No. 37, p. 13635-13639, "Engineering RNA sequence specificity of Pumilio repeats."
Tilsner et al. The Plant Journal 2009, vol. 57, p. 758-770, "Live-cell imaging of viral RNA genomes using a Pumilio-based reporter."
Hook et al. RNA 2005, vol. 11, p. 227-233, "RNA-protein interactions in the yeast three-hybrid system: Affinity, sensitivity, and enhanced library screening."
Thomson et al. RNA 2007, vol. 13, p. 2165-2174, "Nop9 is an RNA binding protein present in pre-40S ribosomes and required for 18S rRNA synthesis in yeast."
Gerber et al. PLoS Biology Mar. 2004, vol. 2, Issue 3, p. 0342-0354, "Extensive Association of Functionally and Cytotopically Related mRNAs with Puf Family RNA-Binding Proteins in Yeast."
Zhu et al. PNAS Dec. 1, 2009, vol. 106, No. 48, p. 20192-20197, "A 5' cytosine binding pocket in Puf3p specifies regulation of mitochondrial mRNAs."
Koh et al. RNA 2009, vol. 15, p. 1090-1099, "A single C. elegans PUF protein binds RNA in multiple modes."
Filipovska et al. Nature Chemical Biology Jul. 2011, vol. 7, p. 425-427, "A universal code for RNA recognition by PUF proteins."
Dong et al. The Journal of Biological Chemistry 2011, vol. 286, p. 26732-26742, "Specific and Modular Binding Code for Cytosine Recognition in Pumilio/ FBF (PUF) RNA-binding Domains."
Brukner et al. Biochemistry 2000, vol. 39, p. 11463-11466, "Cellular Proteins Prevent Antisense Phosphorothioate Oligonucleotide (SdT18) to Target Sense RNA (rA18): Development of a New in Vitro Assay."
Cassiday et al. Biochemsitry 2001, vol. 40, p. 2433-2438, "In Vivo Recognition of an RNA Aptamer by Its Transcription Factor Target."
Gietz et al. Methods in Enzymology 2002, vol. 350, p. 87-96, "Transformation of Yeast by Lithium Acetate/Single-Stranded Carrier DNA/Polyethylene Glycol Method."

(Continued)

*Primary Examiner* — Richard Hutson
(74) *Attorney, Agent, or Firm* — Brooks Kushman P.C.

(57) ABSTRACT

A recombinant polypeptide is described including at least one PUF RNA-binding domain capable of specifically binding to a cytosine RNA base. The PUF RNA-binding domain of the polypeptide includes at least one RNA base-binding motif of the general formula $X_1X_2X_3X_4X_5X_6X_7X_8X_9X_{10}X_{11}$ wherein $X_1$ is selected from a defined group and wherein the RNA base-binding motif is operably capable of specifically binding to a cytosine RNA base.

11 Claims, 7 Drawing Sheets

(56) References Cited

OTHER PUBLICATIONS

Lund et al. Cold Spring Harb Symp Quant Biol 2006, vol. 71, p. 59-66, "Substrate Selectivity of Exportin 5 and Dicer in the Biogenesis of MicroRNAs."
Ozawa et al. Nature Methods May 2007, vol. 4, No. 5, p. 413-419, "Imaging dynamics of endogenous mitochondrial RNA in single living cells."
Stein., Nature Medicine Nov. 1995, vol. 1, No. 11, p. 1119-1121, "Does Antisense Exist?"
Stumpf et al. Methods in Enzymology 2008, vol. 449, p. 295-315, "Analysis of RNA-Protein Interactions Using a Yeast Three-Hybrid System."
Wang et al. Nature Methods Nov. 2009, vol. 6, No. 11, p. 825-830, "Engineering splicing factors with designed specificities."
Ito et al. PNAS Feb. 1, 2000, vol. 97, No. 3, p. 1143-1147, "Toward a protein-protein interaction map of the budding yeast: A comprehensive system to examine two-hybrid interactions in all possible combinations between the yeast proteins."
Rackham et al. Nature Chemical Biology Aug. 2005, vol. 1, No. 3, p. 159-166, "A network of orthogonal ribosome. mRNA pairs."
Sambrook et al. Molecular Cloning: A Laboratory Manual. Cold Springs Harbor Press 1989, 35 Pages, Table of Contents and Chapter 15, "Expression of Cloned Genes in *Escherichia Coli*."
Sambrook et al. Molecular Cloning: A Laboratory Manual. Cold Springs Harbor Press 1989, 20 Pages, Table of Contents and Chapter 1, "Protocol 17, Directional Cloning into Plasmid Vectors."
Goodwin, E.B., Translational repression: Not just a Puf of smoke, Current Biology 2001, 11:R607-R209.
Lu, G. et al., "Understanding and engineering RNA sequence specificity of PUF proteins," Structural Biology 2009, 19, pp. 110-115.
Spassov, D.S. et al., "The PUF Family of RNA-binding Proteins: Does Evolutionarily Conserved Structure Equal Conserved Function?", Life, 55(7), pp. 359-366, Jul. 2003.
Wickens, M. et al., "A PUF family portrait: 3'UTR regulation as a way of life," Trends in Genetics, v. 18, No. 3, Mar. 2002, pp. 150-157.

\* cited by examiner

"GR"
GRSRLLEDFRNNRYPNLQLREIAG
HIMEFSQDQHGSRFIQLKLERATPAERQLVFNEILQ
AAYQLMVDVFGNYVIQKFFEFGSLEQKLALAERIRG
HVLSLALQMYGCRVIQKALEFIPSDQQVINEMVRELDG
HVLKCVKDQNGNHVVQKCIECVQPQSLQFIIDAFKG
QVFALSTHPYGCRVIQRILEHCLPDQTLPILEELHQ
HTEQLVQDQYGGYVIRHVLEHGRPEDKSKIVAEIRG
NVLVLSQHKFASNVVEKCVTHASRTERAVLIDEVCTMNDGPHS
ALYTMMKDQYANYVVQKMIDVAEPGQRKIVMHKIRP
HIATLRKYTYGKHILAKLEKYYMKNGVDLG

"AR"
GRSRLLEDFRNNRYPNLQLREIAG
HIMEFSQDQHGSRFIQLKLERATPAERQLVFNEILQ
AAYQLMVDVFGNYVIQKFFEFGSLEQKLALAERIRG
HVLSLALQMYGCRVIQKALEFIPSDQQVINEMVRELDG
HVLKCVKDQNGNHVVQKCIECVQPQSLQFIIDAFKG
QVFALSTHPYGCRVIQRILEHCLPDQTLPILEELHQ
HTEQLVQDQYGAYVIRHVLEHGRPEDKSKIVAEIRG
NVLVLSQHKFASNVVEKCVTHASRTERAVLIDEVCTMNDGPHS
ALYTMMKDQYANYVVQKMIDVAEPGQRKIVMHKIRP
HIATLRKYTYGKHILAKLEKYYMKNGVDLG

"SR"
GRSRLLEDFRNNRYPNLQLREIAG
HIMEFSQDQHGSRFIQLKLERATPAERQLVFNEILQ
AAYQLMVDVFGNYVIQKFFEFGSLEQKLALAERIRG
HVLSLALQMYGCRVIQKALEFIPSDQQVINEMVRELDG
HVLKCVKDQNGNHVVQKCIECVQPQSLQFIIDAFKG
QVFALSTHPYGCRVIQRILEHCLPDQTLPILEELHQ
HTEQLVQDQYGSYVIRHVLEHGRPEDKSKIVAEIRG
NVLVLSQHKFASNVVEKCVTHASRTERAVLIDEVCTMNDGPHS
ALYTMMKDQYANYVVQKMIDVAEPGQRKIVMHKIRP
HIATLRKYTYGKHILAKLEKYYMKNGVDLG

"TR"
GRSRLLEDFRNNRYPNLQLREIAG
HIMEFSQDQHGSRFIQLKLERATPAERQLVFNEILQ
AAYQLMVDVFGNYVIQKFFEFGSLEQKLALAERIRG
HVLSLALQMYGCRVIQKALEFIPSDQQVINEMVRELDG
HVLKCVKDQNGNHVVQKCIECVQPQSLQFIIDAFKG
QVFALSTHPYGCRVIQRILEHCLPDQTLPILEELHQ
HTEQLVQDQYGTYVIRHVLEHGRPEDKSKIVAEIRG
NVLVLSQHKFASNVVEKCVTHASRTERAVLIDEVCTMNDGPHS
ALYTMMKDQYANYVVQKMIDVAEPGQRKIVMHKIRP
HIATLRKYTYGKHILAKLEKYYMKNGVDLG

"CR"
GRSRLLEDFRNNRYPNLQLREIAG
HIMEFSQDQHGSRFIQLKLERATPAERQLVFNEILQ
AAYQLMVDVFGNYVIQKFFEFGSLEQKLALAERIRG
HVLSLALQMYGCRVIQKALEFIPSDQQVINEMVRELDG
HVLKCVKDQNGNHVVQKCIECVQPQSLQFIIDAFKG
QVFALSTHPYGCRVIQRILEHCLPDQTLPILEELHQ

HTEQLVQDQYGCYVIRHVLEHGRPEDKSKIVAEIRG
NVLVLSQHKFASNVVEKCVTHASRTERAVLIDEVCTMNDGPHS
ALYTMMKDQYANYVVQKMIDVAEPGQRKIVMHKIRP
HIATLRKYTYGKHILAKLEKYYMKNGVDLG

Figure 7

SEQUENCE LISTING

```
<160> NUMBER OF SEQ ID NOS: 62

<210> SEQ ID NO 1
<211> LENGTH: 11
<212> TYPE: PRT
<213> ORGANISM: Artificial Sequence
<220> FEATURE:
<223> OTHER INFORMATION: Recombinant

<400> SEQUENCE: 1

Gln Tyr Gly Gly Tyr Val Ile Arg His Val Leu
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Recombinant

<400> SEQUENCE: 2

Gln Tyr Gly Ala Tyr Val Ile Arg His Val Leu
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Recombinant

<400> SEQUENCE: 3

Gln Tyr Gly Ser Tyr Val Ile Arg His Val Leu
1               5                   10

<210> SEQ ID NO 4
<211> LENGTH: 11
```

```
<212> TYPE: PRT
<213> ORGANISM: Artificial Sequence
<220> FEATURE:
<223> OTHER INFORMATION: Recombinant

<400> SEQUENCE: 4

Gln Tyr Gly Thr Tyr Val Ile Arg His Val Leu
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Recombinant

<400> SEQUENCE: 5

Gln Tyr Gly Cys Tyr Val Ile Arg His Val Leu
1               5                   10

<210> SEQ ID NO 6
<211> LENGTH: 11
<212> TYPE: PRT
<213> ORGANISM: Homo sapiens

<400> SEQUENCE: 6

Gln His Gly Ser Arg Phe Ile Gln Leu Lys Leu
1               5                   10

<210> SEQ ID NO 7
<211> LENGTH: 11
<212> TYPE: PRT
<213> ORGANISM: Homo sapiens

<400> SEQUENCE: 7

Val Phe Gly Asn Tyr Val Ile Gln Lys Phe Phe
1               5                   10

<210> SEQ ID NO 8
<211> LENGTH: 11
<212> TYPE: PRT
<213> ORGANISM: Homo sapiens

<400> SEQUENCE: 8

Met Tyr Gly Cys Arg Val Ile Gln Lys Ala Leu
1               5                   10

<210> SEQ ID NO 9
<211> LENGTH: 11
<212> TYPE: PRT
<213> ORGANISM: Homo sapiens

<400> SEQUENCE: 9

Gln Asn Gly Asn His Val Val Gln Lys Cys Ile
1               5                   10

<210> SEQ ID NO 10
<211> LENGTH: 11
<212> TYPE: PRT
<213> ORGANISM: Homo sapiens

<400> SEQUENCE: 10

Pro Tyr Gly Cys Arg Val Ile Gln Arg Ile Leu
1               5                   10
```

-continued

<210> SEQ ID NO 11
<211> LENGTH: 11
<212> TYPE: PRT
<213> ORGANISM: Homo sapiens

<400> SEQUENCE: 11

Gln Tyr Gly Asn Tyr Val Ile Gln His Val Leu
1               5                   10

<210> SEQ ID NO 12
<211> LENGTH: 11
<212> TYPE: PRT
<213> ORGANISM: Homo sapiens

<400> SEQUENCE: 12

Lys Phe Ala Ser Asn Val Val Glu Lys Cys Val
1               5                   10

<210> SEQ ID NO 13
<211> LENGTH: 11
<212> TYPE: PRT
<213> ORGANISM: Homo sapiens

<400> SEQUENCE: 13

Gln Tyr Ala Asn Tyr Val Val Gln Lys Met Ile
1               5                   10

<210> SEQ ID NO 14
<211> LENGTH: 351
<212> TYPE: PRT
<213> ORGANISM: Artificial Sequence
<220> FEATURE:
<223> OTHER INFORMATION: Recombinant

<400> SEQUENCE: 14

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Val Ile Asn Glu Met
        115                 120                 125

Val Arg Glu Leu Asp Gly His Val Leu Lys Cys Val Lys Asp Gln Asn
    130                 135                 140

Gly Asn His Val Val Gln Lys Cys Ile Glu Cys Val Gln Pro Gln Ser
145                 150                 155                 160

Leu Gln Phe Ile Ile Asp Ala Phe Lys Gly Gln Val Phe Ala Leu Ser
                165                 170                 175

Thr His Pro Tyr Gly Cys Arg Val Ile Gln Arg Ile Leu Glu His Cys
            180                 185                 190

Leu Pro Asp Gln Thr Leu Pro Ile Leu Glu Glu Leu His Gln His Thr 195                 200                 205
Glu Gln Leu Val Gln Asp Gln Tyr Gly Gly Tyr Val Ile Arg His Val
            210                 215                 220

Leu Glu His Gly Arg Pro Glu Asp Lys Ser Lys Ile Val Ala Glu Ile
225                 230                 235                 240

Arg Gly Asn Val Leu Val Leu Ser Gln His Lys Phe Ala Ser Asn Val
                245                 250                 255

Val Glu Lys Cys Val Thr His Ala Ser Arg Thr Glu Arg Ala Val Leu
            260                 265                 270

Ile Asp Glu Val Cys Thr Met Asn Asp Gly Pro His Ser Ala Leu Tyr
            275                 280                 285

Thr Met Met Lys Asp Gln Tyr Ala Asn Tyr Val Val Gln Lys Met Ile
            290                 295                 300

Asp Val Ala Glu Pro Gly Gln Arg Lys Ile Val Met His Lys Ile Arg
305                 310                 315                 320

Pro His Ile Ala Thr Leu Arg Lys Tyr Thr Tyr Gly Lys His Ile Leu
                325                 330                 335

Ala Lys Leu Glu Lys Tyr Tyr Met Lys Asn Gly Val Asp Leu Gly
            340                 345                 350

<210> SEQ ID NO 15
<211> LENGTH: 351
<212> TYPE: PRT
<213> ORGANISM: Artificial Sequence
<220> FEATURE:
<223> OTHER INFORMATION: Recombinant

<400> SEQUENCE: 15

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
                20                  25                  30

Gln His Gly Ser Arg Phe Ile Gln Leu Lys Leu Glu Arg Ala Thr Pro
            35                  40                  45

Ala Glu Arg Gln Leu Val Phe Asn Glu Ile Leu Gln Ala Ala Tyr Gln
        50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Val Ile Asn Glu Met
        115                 120                 125

Val Arg Glu Leu Asp Gly His Val Leu Lys Cys Val Lys Asp Gln Asn
130                 135                 140

Gly Asn His Val Val Gln Lys Cys Ile Glu Cys Val Gln Pro Gln Ser
                145                 150                 155             160

Leu Gln Phe Ile Ile Asp Ala Phe Lys Gly Gln Val Phe Ala Leu Ser
            165                 170                 175

Thr His Pro Tyr Gly Cys Arg Val Ile Gln Arg Ile Leu Glu His Cys
        180                 185                 190

Leu Pro Asp Gln Thr Leu Pro Ile Leu Glu Glu Leu His Gln His Thr
            195                 200                 205

Glu Gln Leu Val Gln Asp Gln Tyr Gly Ala Tyr Val Ile Arg His Val

```
            210                 215                 220
Leu Glu His Gly Arg Pro Glu Asp Lys Ser Lys Ile Val Ala Glu Ile
225                 230                 235                 240

Arg Gly Asn Val Leu Val Leu Ser Gln His Lys Phe Ala Ser Asn Val
                245                 250                 255

Val Glu Lys Cys Val Thr His Ala Ser Arg Thr Glu Arg Ala Val Leu
                260                 265                 270

Ile Asp Glu Val Cys Thr Met Asn Asp Gly Pro His Ser Ala Leu Tyr
            275                 280                 285

Thr Met Met Lys Asp Gln Tyr Ala Asn Tyr Val Val Gln Lys Met Ile
            290                 295                 300

Asp Val Ala Glu Pro Gly Gln Arg Lys Ile Val Met His Lys Ile Arg
305                 310                 315                 320

Pro His Ile Ala Thr Leu Arg Lys Tyr Thr Tyr Gly Lys His Ile Leu
                325                 330                 335

Ala Lys Leu Glu Lys Tyr Tyr Met Lys Asn Gly Val Asp Leu Gly
                340                 345                 350

<210> SEQ ID NO 16
<211> LENGTH: 351
<212> TYPE: PRT
<213> ORGANISM: Artificial Sequence
<220> FEATURE:
<223> OTHER INFORMATION: Recombinant

<400> SEQUENCE: 16

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
                20                  25                  30

Gln His Gly Ser Arg Phe Ile Gln Leu Lys Leu Glu Arg Ala Thr Pro
            35                  40                  45

Ala Glu Arg Gln Leu Val Phe Asn Glu Ile Leu Gln Ala Ala Tyr Gln
        50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
                100                 105                 110

Lys Ala Leu Glu Phe Ile Pro Ser Asp Gln Gln Val Ile Asn Glu Met
            115                 120                 125

Val Arg Glu Leu Asp Gly His Val Leu Lys Cys Val Lys Asp Gln Asn
130                 135                 140

Gly Asn His Val Val Gln Lys Cys Ile Glu Cys Val Gln Pro Gln Ser
145                 150                 155                 160

Leu Gln Phe Ile Ile Asp Ala Phe Lys Gly Gln Val Phe Ala Leu Ser
                165                 170                 175

Thr His Pro Tyr Gly Cys Arg Val Ile Gln Arg Ile Leu Glu His Cys
            180                 185                 190

Leu Pro Asp Gln Thr Leu Pro Ile Leu Glu Glu Leu His Gln His Thr
        195                 200                 205

Glu Gln Leu Val Gln Asp Gln Tyr Gly Ser Tyr Val Ile Arg His Val
    210                 215                 220

Leu Glu His Gly Arg Pro Glu Asp Lys Ser Lys Ile Val Ala Glu Ile
```

```
                    225                 230                 235                 240

Arg Gly Asn Val Leu Val Leu Ser Gln His Lys Phe Ala Ser Asn Val
                    245                 250                 255

Val Glu Lys Cys Val Thr His Ala Ser Arg Thr Glu Arg Ala Val Leu
                260                 265                 270

Ile Asp Glu Val Cys Thr Met Asn Asp Gly Pro His Ser Ala Leu Tyr
            275                 280                 285

Thr Met Met Lys Asp Gln Tyr Ala Asn Tyr Val Val Gln Lys Met Ile
        290                 295                 300

Asp Val Ala Glu Pro Gly Gln Arg Lys Ile Val Met His Lys Ile Arg
305                 310                 315                 320

Pro His Ile Ala Thr Leu Arg Lys Tyr Thr Tyr Gly Lys His Ile Leu
                325                 330                 335

Ala Lys Leu Glu Lys Tyr Tyr Met Lys Asn Gly Val Asp Leu Gly
                340                 345                 350

<210> SEQ ID NO 17
<211> LENGTH: 351
<212> TYPE: PRT
<213> ORGANISM: Artificial Sequence
<220> FEATURE:
<223> OTHER INFORMATION: Recombinant

<400> SEQUENCE: 17

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
                20                  25                  30

Gln His Gly Ser Arg Phe Ile Gln Leu Lys Leu Glu Arg Ala Thr Pro
            35                  40                  45

Ala Glu Arg Gln Leu Val Phe Asn Glu Ile Leu Gln Ala Ala Tyr Gln
        50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
                100                 105                 110

Lys Ala Leu Glu Phe Ile Pro Ser Asp Gln Gln Val Ile Asn Glu Met
            115                 120                 125

Val Arg Glu Leu Asp Gly His Val Leu Lys Cys Val Lys Asp Gln Asn
        130                 135                 140

Gly Asn His Val Val Gln Lys Cys Ile Glu Cys Val Gln Pro Gln Ser
145                 150                 155                 160

Leu Gln Phe Ile Ile Asp Ala Phe Lys Gly Gln Val Phe Ala Leu Ser
                165                 170                 175

Thr His Pro Tyr Gly Cys Arg Val Ile Gln Arg Ile Leu Glu His Cys
            180                 185                 190

Leu Pro Asp Gln Thr Leu Pro Ile Leu Glu Glu Leu His Gln His Thr
        195                 200                 205

Glu Gln Leu Val Gln Asp Gln Tyr Gly Thr Tyr Val Ile Arg His Val
        210                 215                 220

Leu Glu His Gly Arg Pro Glu Asp Lys Ser Lys Ile Val Ala Glu Ile
225                 230                 235                 240

Arg Gly Asn Val Leu Val Leu Ser Gln His Lys Phe Ala Ser Asn Val
```

```
            245                 250                 255
Val Glu Lys Cys Val Thr His Ala Ser Arg Thr Glu Arg Ala Val Leu
            260                 265                 270

Ile Asp Glu Val Cys Thr Met Asn Asp Gly Pro His Ser Ala Leu Tyr
            275                 280                 285

Thr Met Met Lys Asp Gln Tyr Ala Asn Tyr Val Val Gln Lys Met Ile
            290                 295                 300

Asp Val Ala Glu Pro Gly Gln Arg Lys Ile Val Met His Lys Ile Arg
305                 310                 315                 320

Pro His Ile Ala Thr Leu Arg Lys Tyr Thr Tyr Gly Lys His Ile Leu
                325                 330                 335

Ala Lys Leu Glu Lys Tyr Tyr Met Lys Asn Gly Val Asp Leu Gly
                340                 345                 350
```

<210> SEQ ID NO 18
<211> LENGTH: 351
<212> TYPE: PRT
<213> ORGANISM: Artificial Sequence
<220> FEATURE:
<223> OTHER INFORMATION: Recombinant

<400> SEQUENCE: 18

```
Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
                20                  25                  30

Gln His Gly Ser Arg Phe Ile Gln Leu Lys Leu Glu Arg Ala Thr Pro
            35                  40                  45

Ala Glu Arg Gln Leu Val Phe Asn Glu Ile Leu Gln Ala Ala Tyr Gln
        50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Val Ile Asn Glu Met
        115                 120                 125

Val Arg Glu Leu Asp Gly His Val Leu Lys Cys Val Lys Asp Gln Asn
130                 135                 140

Gly Asn His Val Val Gln Lys Cys Ile Glu Cys Val Gln Pro Gln Ser
145                 150                 155                 160

Leu Gln Phe Ile Ile Asp Ala Phe Lys Gly Gln Val Phe Ala Leu Ser
                165                 170                 175

Thr His Pro Tyr Gly Cys Arg Val Ile Gln Arg Ile Leu Glu His Cys
            180                 185                 190

Leu Pro Asp Gln Thr Leu Pro Ile Leu Glu Glu Leu His Gln His Thr
        195                 200                 205

Glu Gln Leu Val Gln Asp Gln Tyr Gly Cys Tyr Val Ile Arg His Val
    210                 215                 220

Leu Glu His Gly Arg Pro Glu Asp Lys Ser Lys Ile Val Ala Glu Ile
225                 230                 235                 240

Arg Gly Asn Val Leu Val Leu Ser Gln His Lys Phe Ala Ser Asn Val
                245                 250                 255

Val Glu Lys Cys Val Thr His Ala Ser Arg Thr Glu Arg Ala Val Leu
```

| | | 260 | | | | 265 | | | | 270 | | |
|---|---|---|---|---|---|---|---|---|---|---|---|---|
Ile Asp Glu Val Cys Thr Met Asn Asp Gly Pro His Ser Ala Leu Tyr
            275                 280                 285

Thr Met Met Lys Asp Gln Tyr Ala Asn Tyr Val Val Gln Lys Met Ile
            290                 295                 300

Asp Val Ala Glu Pro Gly Gln Arg Lys Ile Val Met His Lys Ile Arg
305                 310                 315                 320

Pro His Ile Ala Thr Leu Arg Lys Tyr Thr Tyr Gly Lys His Ile Leu
                325                 330                 335

Ala Lys Leu Glu Lys Tyr Tyr Met Lys Asn Gly Val Asp Leu Gly
                340                 345                 350

<210> SEQ ID NO 19
<211> LENGTH: 1047
<212> TYPE: DNA
<213> ORGANISM: Artificial Sequence
<220> FEATURE:
<223> OTHER INFORMATION: Recombinant

<400> SEQUENCE: 19
ggtcgtagcc gtctgctgga agattttcgc aataatcgct atccgaatct gcaactgcgt      60
gaaattgccg gtcatattat ggaatttagc caggatcagc atggtagccg ttttattcag     120
ctgaagcttg aacgtgcaac accggcagaa cgtcagctgg tgtttaatga aattctgcaa     180
gcagcatatc agctgatggt tgatgtgttt ggcaactacg tgatccagaa attttttgag     240
tttggcagcc tggaacagaa actggcactg cagaacgta tccgcggtca tgttctgagc     300
ctggcactgc aaatgtatgg ttgtcgtgtt attcagaaag ccctggaatt cattccgagc     360
gatcagcaga tgaaatggt tcgtgaactg gatggtcatg tgctgaaatg tgtgaaagat     420
cagaatggca atcatgttgt gcagaaatgc attgaatgtg ttcagccgca gagcctgcaa     480
tttattatcg atgcctttaa aggtcaggtt tttgcactga gcacccatcc gtacggttgc     540
cgtgtgatcc agcgcattct ggaacattgt ctgccggatc agaccctgcc gattctggaa     600
gagctccatc agcataccga acagctggtt caggatcagt atggaggtta tgtgattcgt     660
catgttctgg aacatggtcg accggaagat aaaagcaaaa tcgtggccga aattcgtggt     720
aatgtgctgg ttctgagcca gcataaattt gccagcaacg tggttgaaaa atgtgttacc     780
catgcaagcc gtaccgaacg tgcagttctg attgatgaag tgtgcaccat gaatgatggg     840
ccccatagcg cactgtatac catgatgaaa gatcagtatg cgaattacgt ggtccagaaa     900
atgattgatg ttgcagaacc gggtcagcgt aaaattgtga tgcataaaat ccgtccgcat     960
attgcaaccc tgcgcaaata tacctatggc aaacacattc tggccaaact ggaaaaatat    1020
tatatgaaaa atggcgtgga cctgggc                                        1047

<210> SEQ ID NO 20
<211> LENGTH: 1047
<212> TYPE: DNA
<213> ORGANISM: Artificial Sequence
<220> FEATURE:
<223> OTHER INFORMATION: Recombinant

<400> SEQUENCE: 20
ggtcgtagcc gtctgctgga agattttcgc aataatcgct atccgaatct gcaactgcgt      60
gaaattgccg gtcatattat ggaatttagc caggatcagc atggtagccg ttttattcag     120
ctgaagcttg aacgtgcaac accggcagaa cgtcagctgg tgtttaatga aattctgcaa     180

| | |
|---|---|
| gcagcatatc agctgatggt tgatgtgttt ggcaactacg tgatccagaa attttttgag | 240 |
| tttggcagcc tggaacagaa actggcactg gcagaacgta tccgcggtca tgttctgagc | 300 |
| ctggcactgc aaatgtatgg ttgtcgtgtt attcagaaag ccctggaatt cattccgagc | 360 |
| gatcagcaga atgaaatggt tcgtgaactg gatggtcatg tgctgaaatg tgtgaaagat | 420 |
| cagaatggca atcatgttgt gcagaaatgc attgaatgtg ttcagccgca gagcctgcaa | 480 |
| tttattatcg atgcctttaa aggtcaggtt tttgcactga gcacccatcc gtacggttgc | 540 |
| cgtgtgatcc agcgcattct ggaacattgt ctgccggatc agaccctgcc gattctggaa | 600 |
| gagctccatc agcataccga acagctggtt caggatcagt atggagctta tgtgattcgt | 660 |
| catgttctgg aacatggtcg accggaagat aaaagcaaaa tcgtggccga aattcgtggt | 720 |
| aatgtgctgg ttctgagcca gcataaattt gccagcaacg tggttgaaaa atgtgttacc | 780 |
| catgcaagcc gtaccgaacg tgcagttctg attgatgaag tgtgcaccat gaatgatggg | 840 |
| ccccatagcg cactgtatac catgatgaaa gatcagtatg cgaattacgt ggtccagaaa | 900 |
| atgattgatg ttgcagaacc gggtcagcgt aaaattgtga tgcataaaat ccgtccgcat | 960 |
| attgcaaccc tgcgcaaata tacctatggc aaacacattc tggccaaact ggaaaaatat | 1020 |
| tatatgaaaa atggcgtgga cctgggc | 1047 |

<210> SEQ ID NO 21
<211> LENGTH: 1047
<212> TYPE: DNA
<213> ORGANISM: Artificial Sequence
<220> FEATURE:
<223> OTHER INFORMATION: Recombinant

<400> SEQUENCE: 21

| | |
|---|---|
| ggtcgtagcc gtctgctgga agattttcgc aataatcgct atccgaatct gcaactgcgt | 60 |
| gaaattgccg gtcatattat ggaatttagc caggatcagc atggtagccg ttttattcag | 120 |
| ctgaagcttg aacgtgcaac accggcagaa cgtcagctgg tgtttaatga aattctgcaa | 180 |
| gcagcatatc agctgatggt tgatgtgttt ggcaactacg tgatccagaa attttttgag | 240 |
| tttggcagcc tggaacagaa actggcactg gcagaacgta tccgcggtca tgttctgagc | 300 |
| ctggcactgc aaatgtatgg ttgtcgtgtt attcagaaag ccctggaatt cattccgagc | 360 |
| gatcagcaga atgaaatggt tcgtgaactg gatggtcatg tgctgaaatg tgtgaaagat | 420 |
| cagaatggca atcatgttgt gcagaaatgc attgaatgtg ttcagccgca gagcctgcaa | 480 |
| tttattatcg atgcctttaa aggtcaggtt tttgcactga gcacccatcc gtacggttgc | 540 |
| cgtgtgatcc agcgcattct ggaacattgt ctgccggatc agaccctgcc gattctggaa | 600 |
| gagctccatc agcataccga acagctggtt caggatcagt atggatctta tgtgattcgt | 660 |
| catgttctgg aacatggtcg accggaagat aaaagcaaaa tcgtggccga aattcgtggt | 720 |
| aatgtgctgg ttctgagcca gcataaattt gccagcaacg tggttgaaaa atgtgttacc | 780 |
| catgcaagcc gtaccgaacg tgcagttctg attgatgaag tgtgcaccat gaatgatggg | 840 |
| ccccatagcg cactgtatac catgatgaaa gatcagtatg cgaattacgt ggtccagaaa | 900 |
| atgattgatg ttgcagaacc gggtcagcgt aaaattgtga tgcataaaat ccgtccgcat | 960 |
| attgcaaccc tgcgcaaata tacctatggc aaacacattc tggccaaact ggaaaaatat | 1020 |
| tatatgaaaa atggcgtgga cctgggc | 1047 |

<210> SEQ ID NO 22
<211> LENGTH: 1047

```
<212> TYPE: DNA
<213> ORGANISM: Artificial Sequence
<220> FEATURE:
<223> OTHER INFORMATION: Recombinant

<400> SEQUENCE: 22
ggtcgtagcc gtctgctgga agattttcgc aataatcgct atccgaatct gcaactgcgt      60
gaaattgccg gtcatattat ggaatttagc caggatcagc atggtagccg ttttattcag     120
ctgaagcttg aacgtgcaac accggcagaa cgtcagctgg tgtttaatga aattctgcaa     180
gcagcatatc agctgatggt tgatgtgttt ggcaactacg tgatccagaa attttttgag     240
tttggcagcc tggaacagaa actggcactg gcagaacgta ccgcggtca tgttctgagc      300
ctggcactgc aaatgtatgg ttgtcgtgtt attcagaaag ccctggaatt cattccgagc     360
gatcagcaga tgaaatggt tcgtgaactg gatggtcatg tgctgaaatg tgtgaaagat      420
cagaatggca atcatgttgt gcagaaatgc attgaatgtg ttcagccgca gagcctgcaa    480
tttattatcg atgcctttaa aggtcaggtt tttgcactga gcacccatcc gtacggttgc    540
cgtgtgatcc agcgcattct ggaacattgt ctgccggatc agaccctgcc gattctggaa    600
gagctccatc agcataccga acagctggtt caggatcagt atggaactta tgtgattcgt    660
catgttctgg aacatggtcg accggaagat aaaagcaaaa tcgtggccga aattcgtggt    720
aatgtgctgg ttctgagcca gcataaattt gccagcaacg tggttgaaaa atgtgttacc    780
catgcaagcc gtaccgaacg tgcagttctg attgatgaag tgtgcaccat gaatgatggg    840
ccccatagcg cactgtatac catgatgaaa gatcagtatg cgaattacgt ggtccagaaa    900
atgattgatg ttgcagaacc gggtcagcgt aaaattgtga tgcataaaat ccgtccgcat    960
attgcaaccc tgcgcaaata tacctatggc aaacacattc tggccaaact ggaaaaatat  1020
tatatgaaaa atggcgtgga cctgggc                                         1047

<210> SEQ ID NO 23
<211> LENGTH: 1047
<212> TYPE: DNA
<213> ORGANISM: Artificial Sequence
<220> FEATURE:
<223> OTHER INFORMATION: Recombinant

<400> SEQUENCE: 23
ggtcgtagcc gtctgctgga agattttcgc aataatcgct atccgaatct gcaactgcgt      60
gaaattgccg gtcatattat ggaatttagc caggatcagc atggtagccg ttttattcag     120
ctgaagcttg aacgtgcaac accggcagaa cgtcagctgg tgtttaatga aattctgcaa     180
gcagcatatc agctgatggt tgatgtgttt ggcaactacg tgatccagaa attttttgag     240
tttggcagcc tggaacagaa actggcactg gcagaacgta ccgcggtca tgttctgagc      300
ctggcactgc aaatgtatgg ttgtcgtgtt attcagaaag ccctggaatt cattccgagc     360
gatcagcaga tgaaatggt tcgtgaactg gatggtcatg tgctgaaatg tgtgaaagat      420
cagaatggca atcatgttgt gcagaaatgc attgaatgtg ttcagccgca gagcctgcaa    480
tttattatcg atgcctttaa aggtcaggtt tttgcactga gcacccatcc gtacggttgc    540
cgtgtgatcc agcgcattct ggaacattgt ctgccggatc agaccctgcc gattctggaa    600
gagctccatc agcataccga acagctggtt caggatcagt atggatgcta tgtgattcgt    660
catgttctgg aacatggtcg accggaagat aaaagcaaaa tcgtggccga aattcgtggt    720
aatgtgctgg ttctgagcca gcataaattt gccagcaacg tggttgaaaa atgtgttacc    780
```

```
catgcaagcc gtaccgaacg tgcagttctg attgatgaag tgtgcaccat gaatgatggg    840
ccccatagcg cactgtatac catgatgaaa gatcagtatg cgaattacgt ggtccagaaa    900
atgattgatg ttgcagaacc gggtcagcgt aaaattgtga tgcataaaat ccgtccgcat    960
attgcaaccc tgcgcaaata tacctatggc aaacacattc tggccaaact ggaaaaatat   1020
tatatgaaaa atggcgtgga cctgggc                                       1047
```

<210> SEQ ID NO 24
<211> LENGTH: 351
<212> TYPE: PRT
<213> ORGANISM: Artificial Sequence
<220> FEATURE:
<223> OTHER INFORMATION: Recombinant

<400> SEQUENCE: 24

```
Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Gly Arg Phe Ile Arg Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Val Ile Asn Glu Met
        115                 120                 125

Val Arg Glu Leu Asp Gly His Val Leu Lys Cys Val Lys Asp Gln Asn
    130                 135                 140

Gly Asn His Val Val Gln Lys Cys Ile Glu Cys Val Gln Pro Gln Ser
145                 150                 155                 160

Leu Gln Phe Ile Ile Asp Ala Phe Lys Gly Gln Val Phe Ala Leu Ser
                165                 170                 175

Thr His Pro Tyr Gly Cys Arg Val Ile Gln Arg Ile Leu Glu His Cys
            180                 185                 190

Leu Pro Asp Gln Thr Leu Pro Ile Leu Glu Glu Leu His Gln His Thr
        195                 200                 205

Glu Gln Leu Val Gln Asp Gln Tyr Gly Asn Tyr Val Ile Gln His Val
    210                 215                 220

Leu Glu His Gly Arg Pro Glu Asp Lys Ser Lys Ile Val Ala Glu Ile
225                 230                 235                 240

Arg Gly Asn Val Leu Val Leu Ser Gln His Lys Phe Ala Ser Asn Val
                245                 250                 255

Val Glu Lys Cys Val Thr His Ala Ser Arg Thr Glu Arg Ala Val Leu
            260                 265                 270

Ile Asp Glu Val Cys Thr Met Asn Asp Gly Pro His Ser Ala Leu Tyr
        275                 280                 285

Thr Met Met Lys Asp Gln Tyr Ala Asn Tyr Val Val Gln Lys Met Ile
    290                 295                 300

Asp Val Ala Glu Pro Gly Gln Arg Lys Ile Val Met His Lys Ile Arg
305                 310                 315                 320
```

```
Pro His Ile Ala Thr Leu Arg Lys Tyr Thr Tyr Gly Lys His Ile Leu
                325                 330                 335

Ala Lys Leu Glu Lys Tyr Tyr Met Lys Asn Gly Val Asp Leu Gly
            340                 345                 350

<210> SEQ ID NO 25
<211> LENGTH: 351
<212> TYPE: PRT
<213> ORGANISM: Artificial Sequence
<220> FEATURE:
<223> OTHER INFORMATION: Recombinant

<400> SEQUENCE: 25

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Gly Tyr Val Ile Arg Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Val Ile Asn Glu Met
        115                 120                 125

Val Arg Glu Leu Asp Gly His Val Leu Lys Cys Val Lys Asp Gln Asn
130                 135                 140

Gly Asn His Val Val Gln Lys Cys Ile Glu Cys Val Gln Pro Gln Ser
145                 150                 155                 160

Leu Gln Phe Ile Ile Asp Ala Phe Lys Gly Gln Val Phe Ala Leu Ser
                165                 170                 175

Thr His Pro Tyr Gly Cys Arg Val Ile Gln Arg Ile Leu Glu His Cys
            180                 185                 190

Leu Pro Asp Gln Thr Leu Pro Ile Leu Glu Glu Leu His Gln His Thr
        195                 200                 205

Glu Gln Leu Val Gln Asp Gln Tyr Gly Asn Tyr Val Ile Gln His Val
    210                 215                 220

Leu Glu His Gly Arg Pro Glu Asp Lys Ser Lys Ile Val Ala Glu Ile
225                 230                 235                 240

Arg Gly Asn Val Leu Val Leu Ser Gln His Lys Phe Ala Ser Asn Val
                245                 250                 255

Val Glu Lys Cys Val Thr His Ala Ser Arg Thr Glu Arg Ala Val Leu
            260                 265                 270

Ile Asp Glu Val Cys Thr Met Asn Asp Gly Pro His Ser Ala Leu Tyr
        275                 280                 285

Thr Met Met Lys Asp Gln Tyr Ala Asn Tyr Val Val Gln Lys Met Ile
    290                 295                 300

Asp Val Ala Glu Pro Gly Gln Arg Lys Ile Val Met His Lys Ile Arg
305                 310                 315                 320

Pro His Ile Ala Thr Leu Arg Lys Tyr Thr Tyr Gly Lys His Ile Leu
                325                 330                 335
```

```
<210> SEQ ID NO 26
<211> LENGTH: 351
<212> TYPE: PRT
<213> ORGANISM: Artificial Sequence
<220> FEATURE:
<223> OTHER INFORMATION: Recombinant

<400> SEQUENCE: 26

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Gly Arg Val Ile Arg
            100                 105                 110

Lys Ala Leu Glu Phe Ile Pro Ser Asp Gln Gln Val Ile Asn Glu Met
        115                 120                 125

Val Arg Glu Leu Asp Gly His Val Leu Lys Cys Val Lys Asp Gln Asn
    130                 135                 140

Gly Asn His Val Val Gln Lys Cys Ile Glu Cys Val Gln Pro Gln Ser
145                 150                 155                 160

Leu Gln Phe Ile Ile Asp Ala Phe Lys Gly Gln Val Phe Ala Leu Ser
                165                 170                 175

Thr His Pro Tyr Gly Cys Arg Val Ile Gln Arg Ile Leu Glu His Cys
            180                 185                 190

Leu Pro Asp Gln Thr Leu Pro Ile Leu Glu Glu Leu His Gln His Thr
        195                 200                 205

Glu Gln Leu Val Gln Asp Gln Tyr Gly Asn Tyr Val Ile Gln His Val
    210                 215                 220

Leu Glu His Gly Arg Pro Glu Asp Lys Ser Lys Ile Val Ala Glu Ile
225                 230                 235                 240

Arg Gly Asn Val Leu Val Leu Ser Gln His Lys Phe Ala Ser Asn Val
                245                 250                 255

Val Glu Lys Cys Val Thr His Ala Ser Arg Thr Glu Arg Ala Val Leu
            260                 265                 270

Ile Asp Glu Val Cys Thr Met Asn Asp Gly Pro His Ser Ala Leu Tyr
        275                 280                 285

Thr Met Met Lys Asp Gln Tyr Ala Asn Tyr Val Val Gln Lys Met Ile
    290                 295                 300

Asp Val Ala Glu Pro Gly Gln Arg Lys Ile Val Met His Lys Ile Arg
305                 310                 315                 320

Pro His Ile Ala Thr Leu Arg Lys Tyr Thr Tyr Gly Lys His Ile Leu
                325                 330                 335

Ala Lys Leu Glu Lys Tyr Tyr Met Lys Asn Gly Val Asp Leu Gly
            340                 345                 350
```

```
<210> SEQ ID NO 27
<211> LENGTH: 351
<212> TYPE: PRT
<213> ORGANISM: Artificial Sequence
<220> FEATURE:
<223> OTHER INFORMATION: Recombinant

<400> SEQUENCE: 27
```

| | | | | | | | | | | | | | | | |
|---|---|---|---|---|---|---|---|---|---|---|---|---|---|---|---|
| Gly | Arg | Ser | Arg | Leu | Leu | Glu | Asp | Phe | Arg | Asn | Asn | Arg | Tyr | Pro | Asn |
| 1 | | | | 5 | | | | | 10 | | | | | 15 | |
| Leu | Gln | Leu | Arg | Glu | Ile | Ala | Gly | His | Ile | Met | Glu | Phe | Ser | Gln | Asp |
| | | | 20 | | | | | 25 | | | | | 30 | | |
| Gln | His | Gly | Ser | Arg | Phe | Ile | Gln | Leu | Lys | Leu | Glu | Arg | Ala | Thr | Pro |
| | | | 35 | | | | | 40 | | | | | 45 | | |
| Ala | Glu | Arg | Gln | Leu | Val | Phe | Asn | Glu | Ile | Leu | Gln | Ala | Ala | Tyr | Gln |
| | | 50 | | | | | 55 | | | | | 60 | | | |
| Leu | Met | Val | Asp | Val | Phe | Gly | Asn | Tyr | Val | Ile | Gln | Lys | Phe | Phe | Glu |
| 65 | | | | | 70 | | | | | 75 | | | | | 80 |
| Phe | Gly | Ser | Leu | Glu | Gln | Lys | Leu | Ala | Leu | Ala | Glu | Arg | Ile | Arg | Gly |
| | | | | 85 | | | | | 90 | | | | | 95 | |
| His | Val | Leu | Ser | Leu | Ala | Leu | Gln | Met | Tyr | Gly | Cys | Arg | Val | Ile | Gln |
| | | | 100 | | | | | 105 | | | | | 110 | | |
| Lys | Ala | Leu | Glu | Phe | Ile | Pro | Ser | Asp | Gln | Gln | Val | Ile | Asn | Glu | Met |
| | | | 115 | | | | | 120 | | | | | 125 | | |
| Val | Arg | Glu | Leu | Asp | Gly | His | Val | Leu | Lys | Cys | Val | Lys | Asp | Gln | Asn |
| | | 130 | | | | | 135 | | | | | 140 | | | |
| Gly | Gly | His | Val | Val | Arg | Lys | Cys | Ile | Glu | Cys | Val | Gln | Pro | Gln | Ser |
| 145 | | | | | 150 | | | | | 155 | | | | | 160 |
| Leu | Gln | Phe | Ile | Ile | Asp | Ala | Phe | Lys | Gly | Gln | Val | Phe | Ala | Leu | Ser |
| | | | | 165 | | | | | 170 | | | | | 175 | |
| Thr | His | Pro | Tyr | Gly | Cys | Arg | Val | Ile | Gln | Arg | Ile | Leu | Glu | His | Cys |
| | | | 180 | | | | | 185 | | | | | 190 | | |
| Leu | Pro | Asp | Gln | Thr | Leu | Pro | Ile | Leu | Glu | Glu | Leu | His | Gln | His | Thr |
| | | | 195 | | | | | 200 | | | | | 205 | | |
| Glu | Gln | Leu | Val | Gln | Asp | Gln | Tyr | Gly | Asn | Tyr | Val | Ile | Gln | His | Val |
| | | 210 | | | | | 215 | | | | | 220 | | | |
| Leu | Glu | His | Gly | Arg | Pro | Glu | Asp | Lys | Ser | Lys | Ile | Val | Ala | Glu | Ile |
| 225 | | | | | 230 | | | | | 235 | | | | | 240 |
| Arg | Gly | Asn | Val | Leu | Val | Leu | Ser | Gln | His | Lys | Phe | Ala | Ser | Asn | Val |
| | | | | 245 | | | | | 250 | | | | | 255 | |
| Val | Glu | Lys | Cys | Val | Thr | His | Ala | Ser | Arg | Thr | Glu | Arg | Ala | Val | Leu |
| | | | 260 | | | | | 265 | | | | | 270 | | |
| Ile | Asp | Glu | Val | Cys | Thr | Met | Asn | Asp | Gly | Pro | His | Ser | Ala | Leu | Tyr |
| | | | 275 | | | | | 280 | | | | | 285 | | |
| Thr | Met | Met | Lys | Asp | Gln | Tyr | Ala | Asn | Tyr | Val | Val | Gln | Lys | Met | Ile |
| | | 290 | | | | | 295 | | | | | 300 | | | |
| Asp | Val | Ala | Glu | Pro | Gly | Gln | Arg | Lys | Ile | Val | Met | His | Lys | Ile | Arg |
| 305 | | | | | 310 | | | | | 315 | | | | | 320 |
| Pro | His | Ile | Ala | Thr | Leu | Arg | Lys | Tyr | Thr | Tyr | Gly | Lys | His | Ile | Leu |
| | | | | 325 | | | | | 330 | | | | | 335 | |
| Ala | Lys | Leu | Glu | Lys | Tyr | Tyr | Met | Lys | Asn | Gly | Val | Asp | Leu | Gly | |
| | | | 340 | | | | | 345 | | | | | 350 | | |

```
<210> SEQ ID NO 28
```

<211> LENGTH: 351
<212> TYPE: PRT
<213> ORGANISM: Artificial Sequence
<220> FEATURE:
<223> OTHER INFORMATION: Recombinant

<400> SEQUENCE: 28

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Val Ile Asn Glu Met
        115                 120                 125

Val Arg Glu Leu Asp Gly His Val Leu Lys Cys Val Lys Asp Gln Asn
130                 135                 140

Gly Asn His Val Val Gln Lys Cys Ile Glu Cys Val Gln Pro Gln Ser
145                 150                 155                 160

Leu Gln Phe Ile Ile Asp Ala Phe Lys Gly Gln Val Phe Ala Leu Ser
                165                 170                 175

Thr His Pro Tyr Gly Gly Arg Val Ile Arg Arg Ile Leu Glu His Cys
            180                 185                 190

Leu Pro Asp Gln Thr Leu Pro Ile Leu Glu Glu Leu His Gln His Thr
        195                 200                 205

Glu Gln Leu Val Gln Asp Gln Tyr Gly Asn Tyr Val Ile Gln His Val
    210                 215                 220

Leu Glu His Gly Arg Pro Glu Asp Lys Ser Lys Ile Val Ala Glu Ile
225                 230                 235                 240

Arg Gly Asn Val Leu Val Leu Ser Gln His Lys Phe Ala Ser Asn Val
                245                 250                 255

Val Glu Lys Cys Val Thr His Ala Ser Arg Thr Glu Arg Ala Val Leu
            260                 265                 270

Ile Asp Glu Val Cys Thr Met Asn Asp Gly Pro His Ser Ala Leu Tyr
        275                 280                 285

Thr Met Met Lys Asp Gln Tyr Ala Asn Tyr Val Val Gln Lys Met Ile
    290                 295                 300

Asp Val Ala Glu Pro Gly Gln Arg Lys Ile Val Met His Lys Ile Arg
305                 310                 315                 320

Pro His Ile Ala Thr Leu Arg Lys Tyr Thr Tyr Gly Lys His Ile Leu
                325                 330                 335

Ala Lys Leu Glu Lys Tyr Tyr Met Lys Asn Gly Val Asp Leu Gly
            340                 345                 350

<210> SEQ ID NO 29
<211> LENGTH: 351
<212> TYPE: PRT
<213> ORGANISM: Artificial Sequence
<220> FEATURE:
<223> OTHER INFORMATION: Recombinant

<400> SEQUENCE: 29

```
Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Val Ile Asn Glu Met
        115                 120                 125

Val Arg Glu Leu Asp Gly His Val Leu Lys Cys Val Lys Asp Gln Asn
    130                 135                 140

Gly Asn His Val Val Gln Lys Cys Ile Glu Cys Val Gln Pro Gln Ser
145                 150                 155                 160

Leu Gln Phe Ile Ile Asp Ala Phe Lys Gly Gln Val Phe Ala Leu Ser
                165                 170                 175

Thr His Pro Tyr Gly Cys Arg Val Ile Gln Arg Ile Leu Glu His Cys
            180                 185                 190

Leu Pro Asp Gln Thr Leu Pro Ile Leu Glu Glu Leu His Gln His Thr
        195                 200                 205

Glu Gln Leu Val Gln Asp Gln Tyr Gly Asn Tyr Val Ile Gln His Val
    210                 215                 220

Leu Glu His Gly Arg Pro Glu Asp Lys Ser Lys Ile Val Ala Glu Ile
225                 230                 235                 240

Arg Gly Asn Val Leu Val Leu Ser Gln His Lys Phe Ala Gly Asn Val
                245                 250                 255

Val Arg Lys Cys Val Thr His Ala Ser Arg Thr Glu Arg Ala Val Leu
            260                 265                 270

Ile Asp Glu Val Cys Thr Met Asn Asp Gly Pro His Ser Ala Leu Tyr
        275                 280                 285

Thr Met Met Lys Asp Gln Tyr Ala Asn Tyr Val Val Gln Lys Met Ile
    290                 295                 300

Asp Val Ala Glu Pro Gly Gln Arg Lys Ile Val Met His Lys Ile Arg
305                 310                 315                 320

Pro His Ile Ala Thr Leu Arg Lys Tyr Thr Tyr Gly Lys His Ile Leu
                325                 330                 335

Ala Lys Leu Glu Lys Tyr Tyr Met Lys Asn Gly Val Asp Leu Gly
            340                 345                 350
```

<210> SEQ ID NO 30
<211> LENGTH: 351
<212> TYPE: PRT
<213> ORGANISM: Artificial Sequence
<220> FEATURE:
<223> OTHER INFORMATION: Recombinant

<400> SEQUENCE: 30

Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Val Ile Asn Glu Met
        115                 120                 125

Val Arg Glu Leu Asp Gly His Val Leu Lys Cys Val Lys Asp Gln Asn
    130                 135                 140

Gly Asn His Val Val Gln Lys Cys Ile Glu Cys Val Gln Pro Gln Ser
145                 150                 155                 160

Leu Gln Phe Ile Ile Asp Ala Phe Lys Gly Gln Val Phe Ala Leu Ser
                165                 170                 175

Thr His Pro Tyr Gly Cys Arg Val Ile Gln Arg Ile Leu Glu His Cys
            180                 185                 190

Leu Pro Asp Gln Thr Leu Pro Ile Leu Glu Glu Leu His Gln His Thr
        195                 200                 205

Glu Gln Leu Val Gln Asp Gln Tyr Gly Asn Tyr Val Ile Gln His Val
    210                 215                 220

Leu Glu His Gly Arg Pro Glu Asp Lys Ser Lys Ile Val Ala Glu Ile
225                 230                 235                 240

Arg Gly Asn Val Leu Val Leu Ser Gln His Lys Phe Ala Ser Asn Val
                245                 250                 255

Val Glu Lys Cys Val Thr His Ala Ser Arg Thr Glu Arg Ala Val Leu
            260                 265                 270

Ile Asp Glu Val Cys Thr Met Asn Asp Gly Pro His Ser Ala Leu Tyr
        275                 280                 285

Thr Met Met Lys Asp Gln Tyr Ala Gly Tyr Val Val Arg Lys Met Ile
    290                 295                 300

Asp Val Ala Glu Pro Gly Gln Arg Lys Ile Val Met His Lys Ile Arg
305                 310                 315                 320

Pro His Ile Ala Thr Leu Arg Lys Tyr Thr Tyr Gly Lys His Ile Leu
                325                 330                 335

Ala Lys Leu Glu Lys Tyr Tyr Met Lys Asn Gly Val Asp Leu Gly
            340                 345                 350

<210> SEQ ID NO 31
<211> LENGTH: 1047
<212> TYPE: DNA
<213> ORGANISM: Artificial Sequence
<220> FEATURE:
<223> OTHER INFORMATION: Recombinant

<400> SEQUENCE: 31
ggtcgtagcc gtctgctgga agattttcgc aataatcgct atccgaatct gcaactgcgt    60

```
gaaattgccg gtcatattat ggaatttagc caggatcagc atggtggtcg ttttattcgt    120
ctgaagcttg aacgtgcaac accggcagaa cgtcagctgg tgtttaatga aattctgcaa    180
gcagcatatc agctgatggt tgatgtgttt ggcaactacg tgatccagaa attttttgag    240
tttggcagcc tggaacagaa actggcactg gcagaacgta ccgcggtca tgttctgagc     300 ctggcactgc aaatgtatgg ttgtcgtgtt attcagaaag ccctggaatt cattccgagc    360
gatcagcaga tgaaatggt tcgtgaactg atggtcatg tgctgaaatg tgtgaaagat      420
cagaatggca atcatgttgt gcagaaatgc attgaatgtg ttcagccgca gagcctgcaa    480
tttattatcg atgcctttaa aggtcaggtt tttgcactga gcacccatcc gtacggttgc    540
cgtgtgatcc agcgcattct ggaacattgt ctgccggatc agaccctgcc gattctggaa    600
gagctccatc agcataccga acagctggtt caggatcagt atggaaacta tgtgattcag    660
catgttctgg aacatggtcg accggaagat aaaagcaaaa tcgtggccga aattcgtggt    720
aatgtgctgt tcctgagcca gcataaattt gccagcaacg tggttgaaaa atgtgttacc    780
catgcaagcc gtaccgaacg tgcagttctg attgatgaag tgtgcaccat gaatgatggg    840
ccccatagcg cactgtatac catgatgaaa gatcagtatg cgaattacgt ggtccagaaa    900
atgattgatg ttgcagaacc gggtcagcgt aaaattgtga tgcataaaat ccgtccgcat    960
attgcaaccc tgcgcaaata tacctatggc aaacacattc tggccaaact ggaaaaatat   1020
tatatgaaaa atggcgtgga cctgggc                                       1047

<210> SEQ ID NO 32
<211> LENGTH: 1047
<212> TYPE: DNA
<213> ORGANISM: Artificial Sequence
<220> FEATURE:
<223> OTHER INFORMATION: Recombinant

<400> SEQUENCE: 32
ggtcgtagcc gtctgctgga agattttcgc aataatcgct atccgaatct gcaactgcgt     60
gaaattgccg gtcatattat ggaatttagc caggatcagc atggtagccg ttttattcag    120
ctgaagcttg aacgtgcaac accggcagaa cgtcagctgg tgtttaatga aattctgcaa    180
gcagcatatc agctgatggt tgatgtgttt ggcggttacg tgatccgtaa attttttgag    240
tttggcagcc tggaacagaa actggcactg gcagaacgta ccgcggtca tgttctgagc     300 ctggcactgc aaatgtatgg ttgtcgtgtt attcagaaag ccctggaatt cattccgagc    360
gatcagcaga tgaaatggt tcgtgaactg atggtcatg tgctgaaatg tgtgaaagat      420
cagaatggca atcatgttgt gcagaaatgc attgaatgtg ttcagccgca gagcctgcaa    480
tttattatcg atgcctttaa aggtcaggtt tttgcactga gcacccatcc gtacggttgc    540
cgtgtgatcc agcgcattct ggaacattgt ctgccggatc agaccctgcc gattctggaa    600
gagctccatc agcataccga acagctggtt caggatcagt atggaaacta tgtgattcag    660
catgttctgg aacatggtcg accggaagat aaaagcaaaa tcgtggccga aattcgtggt    720
aatgtgctgg ttcctgagcca gcataaattt gccagcaacg tggttgaaaa atgtgttacc   780
catgcaagcc gtaccgaacg tgcagttctg attgatgaag tgtgcaccat gaatgatggg    840
ccccatagcg cactgtatac catgatgaaa gatcagtatg cgaattacgt ggtccagaaa    900
atgattgatg ttgcagaacc gggtcagcgt aaaattgtga tgcataaaat ccgtccgcat    960
attgcaaccc tgcgcaaata tacctatggc aaacacattc tggccaaact ggaaaaatat   1020
```

```
tatatgaaaa atggcgtgga cctgggc                                         1047

<210> SEQ ID NO 33
<211> LENGTH: 1047
<212> TYPE: DNA
<213> ORGANISM: Artificial Sequence
<220> FEATURE:
<223> OTHER INFORMATION: Recombinant

<400> SEQUENCE: 33
ggtcgtagcc gtctgctgga agattttcgc aataatcgct atccgaatct gcaactgcgt      60
gaaattgccg gtcatattat ggaatttagc caggatcagc atggtagccg ttttattcag     120
ctgaagcttg aacgtgcaac accggcagaa cgtcagctgg tgtttaatga aattctgcaa     180
gcagcatatc agctgatggt tgatgtgttt ggcaactacg tgatccagaa attttttgag     240
tttggcagcc tggaacagaa actggcactg gcagaacgta ccgcggtca tgttctgagc      300 ctggcactgc aaatgtatgg tggtcgtgtt attcgtaaag ccctggaatt cattccgagc     360
gatcagcaga atgaaatggt tcgtgaactg gatggtcatg tgctgaaatg tgtgaaagat     420
cagaatggca atcatgttgt gcagaaatgc attgaatgtg ttcagccgca gagcctgcaa     480
tttattatcg atgcctttaa aggtcaggtt tttgcactga gcacccatcc gtacggttgc     540
cgtgtgatcc agcgcattct ggaacattgt ctgccggatc agaccctgcc gattctggaa     600
gagctccatc agcataccga acagctggtt caggatcagt atgaaacta tgtgattcag      660 catgttctgg aacatggtcg accggaagat aaaagcaaaa tcgtggccga aattcgtggt     720
aatgtgctgg ttctgagcca gcataaattt gccagcaacg tggttgaaaa atgtgttacc     780
catgcaagcc gtaccgaacg tgcagttctg attgatgaag tgtgcaccat gaatgatggg     840
ccccatagcg cactgtatac catgatgaaa atcagtatg cgaattacgt ggtccagaaa      900
atgattgatg ttgcagaacc gggtcagcgt aaaattgtga tgcataaaat ccgtccgcat     960
attgcaaccc tgcgcaaata tacctatggc aaacacattc tggccaaact ggaaaaatat    1020
tatatgaaaa atggcgtgga cctgggc                                        1047

<210> SEQ ID NO 34
<211> LENGTH: 1047
<212> TYPE: DNA
<213> ORGANISM: Artificial Sequence
<220> FEATURE:
<223> OTHER INFORMATION: Recombinant

<400> SEQUENCE: 34
ggtcgtagcc gtctgctgga agattttcgc aataatcgct atccgaatct gcaactgcgt      60
gaaattgccg gtcatattat ggaatttagc caggatcagc atggtagccg ttttattcag     120
ctgaagcttg aacgtgcaac accggcagaa cgtcagctgg tgtttaatga aattctgcaa     180
gcagcatatc agctgatggt tgatgtgttt ggcaactacg tgatccagaa attttttgag     240
tttggcagcc tggaacagaa actggcactg gcagaacgta ccgcggtca tgttctgagc      300 ctggcactgc aaatgtatgg ttgtcgtgtt attcagaaag ccctggaatt cattccgagc     360
gatcagcaga atgaaatggt tcgtgaactg gatggtcatg tgctgaaatg tgtgaaagat     420
cagaatggcg tcatgttgtgt gcgtaaatgc attgaatgtg ttcagccgca gagcctgcaa     480
tttattatcg atgcctttaa aggtcaggtt tttgcactga gcacccatcc gtacggttgc     540
cgtgtgatcc agcgcattct ggaacattgt ctgccggatc agaccctgcc gattctggaa     600
gagctccatc agcataccga acagctggtt caggatcagt atgaaacta tgtgattcag      660
```

```
catgttctgg aacatggtcg accggaagat aaaagcaaaa tcgtggccga aattcgtggt    720
aatgtgctgg ttctgagcca gcataaattt gccagcaacg tggttgaaaa atgtgttacc    780
catgcaagcc gtaccgaacg tgcagttctg attgatgaag tgtgcaccat gaatgatggg    840
ccccatagcg cactgtatac catgatgaaa gatcagtatg cgaattacgt ggtccagaaa    900
atgattgatg ttgcagaacc gggtcagcgt aaaattgtga tgcataaaat ccgtccgcat    960
attgcaaccc tgcgcaaata tacctatggc aaacacattc tggccaaact ggaaaaatat   1020
tatatgaaaa atggcgtgga cctgggc                                       1047
```

<210> SEQ ID NO 35
<211> LENGTH: 1047
<212> TYPE: DNA
<213> ORGANISM: Artificial Sequence
<220> FEATURE:
<223> OTHER INFORMATION: Recombinant

<400> SEQUENCE: 35

```
ggtcgtagcc gtctgctgga agattttcgc aataatcgct atccgaatct gcaactgcgt     60
gaaattgccg gtcatattat ggaatttagc caggatcagc atggtagccg ttttattcag    120
ctgaagcttg aacgtgcaac accggcagaa cgtcagctgg tgtttaatga aattctgcaa    180
gcagcatatc agctgatggt tgatgtgttt ggcaactacg tgatccagaa attttttgag    240
tttggcagcc tggaacagaa actggcactg gcagaacgta tccgcggtca tgttctgagc    300
ctggcactgc aaatgtatgg ttgtcgtgtt attcagaaag ccctggaatt cattccgagc    360
gatcagcaga tgaaatggtc tgtgaactg atggtcatg tgctgaaatg tgtgaaagat    420
cagaatggca atcatgttgt gcagaaatgc attgaatgtg ttcagccgca gagcctgcaa    480
tttattatcg atgcctttaa aggtcaggtt tttgcactga gcacccatcc gtacggtggt    540
cgtgtgatcc gtcgcattct ggaacattgt ctgccggatc agaccctgcc gattctggaa    600
gagctccatc agcataccga acagctggtt caggatcagt atggaaacta tgtgattcag    660
catgttctgg aacatggtcg accggaagat aaaagcaaaa tcgtggccga aattcgtggt    720
aatgtgctgg ttctgagcca gcataaattt gccagcaacg tggttgaaaa atgtgttacc    780
catgcaagcc gtaccgaacg tgcagttctg attgatgaag tgtgcaccat gaatgatggg    840
ccccatagcg cactgtatac catgatgaaa gatcagtatg cgaattacgt ggtccagaaa    900
atgattgatg ttgcagaacc gggtcagcgt aaaattgtga tgcataaaat ccgtccgcat    960
attgcaaccc tgcgcaaata tacctatggc aaacacattc tggccaaact ggaaaaatat   1020
tatatgaaaa atggcgtgga cctgggc                                       1047
```

<210> SEQ ID NO 36
<211> LENGTH: 1047
<212> TYPE: DNA
<213> ORGANISM: Artificial Sequence
<220> FEATURE:
<223> OTHER INFORMATION: Recombinant

<400> SEQUENCE: 36

```
ggtcgtagcc gtctgctgga agattttcgc aataatcgct atccgaatct gcaactgcgt     60
gaaattgccg gtcatattat ggaatttagc caggatcagc atggtagccg ttttattcag    120
ctgaagcttg aacgtgcaac accggcagaa cgtcagctgg tgtttaatga aattctgcaa    180
gcagcatatc agctgatggt tgatgtgttt ggcaactacg tgatccagaa attttttgag    240
```

| | |
|---|---|
| tttggcagcc tggaacagaa actggcactg gcagaacgta ccgcggtca tgttctgagc | 300 |
| ctggcactgc aaatgtatgg ttgtcgtgtt attcagaaag ccctggaatt cattccgagc | 360 |
| gatcagcaga atgaaatggt tcgtgaactg gatggtcatg tgctgaaatg tgtgaaagat | 420 |
| cagaatggca atcatgttgt gcagaaatgc attgaatgtg ttcagccgca gagcctgcaa | 480 |
| tttattatcg atgcctttaa aggtcaggtt tttgcactga gcacccatcc gtacggttgc | 540 |
| cgtgtgatcc agcgcattct ggaacattgt ctgccggatc agaccctgcc gattctggaa | 600 |
| gagctccatc agcataccga acagctggtt caggatcagt atggaaacta tgtgattcag | 660 |
| catgttctgg aacatggtcg accggaagat aaaagcaaaa tcgtggccga attcgtggt | 720 |
| aatgtgctgg ttctgagcca gcataaattt gccggtaacg tggttcgtaa atgtgttacc | 780 |
| catgcaagcc gtaccgaacg tgcagttctg attgatgaag tgtgcaccat gaatgatggg | 840 |
| ccccatagcg cactgtatac catgatgaaa gatcagtatg cgaattacgt ggtccagaaa | 900 |
| atgattgatg ttgcagaacc gggtcagcgt aaaattgtga tgcataaaat ccgtccgcat | 960 |
| attgcaaccc tgcgcaaata tacctatggc aaacacattc tggccaaact ggaaaaatat | 1020 |
| tatatgaaaa atggcgtgga cctgggc | 1047 |

<210> SEQ ID NO 37
<211> LENGTH: 1047
<212> TYPE: DNA
<213> ORGANISM: Artificial Sequence
<220> FEATURE:
<223> OTHER INFORMATION: Recombinant

<400> SEQUENCE: 37

| | |
|---|---|
| ggtcgtagcc gtctgctgga agattttcgc aataatcgct atccgaatct gcaactgcgt | 60 |
| gaaattgccg gtcatattat ggaatttagc caggatcagc atggtagccg ttttattcag | 120 |
| ctgaagcttg aacgtgcaac accggcagaa cgtcagctgg tgtttaatga aattctgcaa | 180 |
| gcagcatatc agctgatggt tgatgtgttt ggcaactacg tgatccagaa attttttgag | 240 |
| tttggcagcc tggaacagaa actggcactg gcagaacgta ccgcggtca tgttctgagc | 300 |
| ctggcactgc aaatgtatgg ttgtcgtgtt attcagaaag ccctggaatt cattccgagc | 360 |
| gatcagcaga atgaaatggt tcgtgaactg gatggtcatg tgctgaaatg tgtgaaagat | 420 |
| cagaatggca atcatgttgt gcagaaatgc attgaatgtg ttcagccgca gagcctgcaa | 480 |
| tttattatcg atgcctttaa aggtcaggtt tttgcactga gcacccatcc gtacggttgc | 540 |
| cgtgtgatcc agcgcattct ggaacattgt ctgccggatc agaccctgcc gattctggaa | 600 |
| gagctccatc agcataccga acagctggtt caggatcagt atggaaacta tgtgattcag | 660 |
| catgttctgg aacatggtcg accggaagat aaaagcaaaa tcgtggccga attcgtggt | 720 |
| aatgtgctgg ttctgagcca gcataaattt gccagcaacg tggttgaaaa atgtgttacc | 780 |
| catgcaagcc gtaccgaacg tgcagttctg attgatgaag tgtgcaccat gaatgatggg | 840 |
| ccccatagcg cactgtatac catgatgaaa gatcagtatg cgggttacgt ggtccgtaaa | 900 |
| atgattgatg ttgcagaacc gggtcagcgt aaaattgtga tgcataaaat ccgtccgcat | 960 |
| attgcaaccc tgcgcaaata tacctatggc aaacacattc tggccaaact ggaaaaatat | 1020 |
| tatatgaaaa atggcgtgga cctgggc | 1047 |

<210> SEQ ID NO 38
<211> LENGTH: 1047
<212> TYPE: DNA
<213> ORGANISM: Homo sapiens

<400> SEQUENCE: 38

```
ggcaggagca ggcttttgga agattttcga acaaccggt accccaattt acaactgcgg      60
gagattgctg acatataat ggaattttcc caagaccagc atgggtccag attcattcag     120
ctgaaactgg agcgtgccac accagctgag cgccagcttg tcttcaatga atcctccag     180
gctgcctacc aactcatggt ggatgtgttt ggtaattacg tcattcagaa gttctttgaa     240
tttggcagtc ttgaacagaa gctggctttg cagaacgga ttcgaggcca cgtcctgtca     300
ttggcactac agatgtatgg ctgccgtgtt atccagaaag ctcttgagtt tattccttca     360
gaccagcaga atgagatggt tcgggaacta gatggccatg tcttgaagtg tgtgaaagat     420
cagaatggca atcacgtggt tcagaaatgc attgaatgtg tacagcccca gtctttgcaa     480
tttatcatcg atgcgtttaa gggacaggta tttgccttat ccacacatcc ttatggctgc     540
cgagtgattc agagaatcct ggagcactgt ctccctgacc agacactccc tattttagag     600
gagcttcacc agcacacaga gcagcttgta caggatcaat atggaaatta tgtaatccaa     660
catgtactgg agcacggtcg tcctgaggat aaaagcaaaa ttgtagcaga atccgaggc     720
aatgtacttg tattgagtca gcacaaattt gcaagcaatg ttgtggagaa gtgtgttact     780
cacgcctcac gtacggagcg cgctgtgctc atcgatgagg tgtgcaccat gaacgacggt     840
ccccacagtg cctatacac catgatgaag accagtatg ccaactacgt ggtccagaag     900
atgattgacg tggcggagcc aggccagcgg aagatcgtca tgcataagat ccggccccac     960
atcgcaactc ttcgtaagta cacctatggc aagcacattc tggccaagct ggagaagtac    1020
tacatgaaga acggtgttga cttaggg                                        1047
```

<210> SEQ ID NO 39
<211> LENGTH: 351
<212> TYPE: PRT
<213> ORGANISM: Homo sapiens

<400> SEQUENCE: 39

```
Gly Arg Ser Arg Leu Leu Glu Asp Phe Arg Asn Asn Arg Tyr Pro Asn
1               5                   10                  15

Leu Gln Leu Arg Glu Ile Ala Gly His Ile Met Glu Phe Ser Gln Asp
            20                  25                  30

Gln His Gly Ser Arg Phe Ile Gln Leu Lys Leu Glu Arg Ala Thr Pro
        35                  40                  45

Ala Glu Arg Gln Leu Val Phe Asn Glu Ile Leu Gln Ala Ala Tyr Gln
    50                  55                  60

Leu Met Val Asp Val Phe Gly Asn Tyr Val Ile Gln Lys Phe Phe Glu
65                  70                  75                  80

Phe Gly Ser Leu Glu Gln Lys Leu Ala Leu Ala Glu Arg Ile Arg Gly
                85                  90                  95

His Val Leu Ser Leu Ala Leu Gln Met Tyr Gly Cys Arg Val Ile Gln
            100                 105                 110

Lys Ala Leu Glu Phe Ile Pro Ser Asp Gln Gln Val Ile Asn Glu Met
        115                 120                 125

Val Arg Glu Leu Asp Gly His Val Leu Lys Cys Val Lys Asp Gln Asn
    130                 135                 140

Gly Asn His Val Val Gln Lys Cys Ile Glu Cys Val Gln Pro Gln Ser
145                 150                 155                 160

Leu Gln Phe Ile Ile Asp Ala Phe Lys Gly Gln Val Phe Ala Leu Ser
                165                 170                 175
```

```
Thr His Pro Tyr Gly Cys Arg Val Ile Gln Arg Ile Leu Glu His Cys
            180                 185                 190
Leu Pro Asp Gln Thr Leu Pro Ile Leu Glu Glu Leu His Gln His Thr
        195                 200                 205
Glu Gln Leu Val Gln Asp Gln Tyr Gly Asn Tyr Val Ile Gln His Val
    210                 215                 220
Leu Glu His Gly Arg Pro Glu Asp Lys Ser Lys Ile Val Ala Glu Ile
225                 230                 235                 240
Arg Gly Asn Val Leu Val Leu Ser Gln His Lys Phe Ala Ser Asn Val
                245                 250                 255
Val Glu Lys Cys Val Thr His Ala Ser Arg Thr Glu Arg Ala Val Leu
            260                 265                 270
Ile Asp Glu Val Cys Thr Met Asn Asp Gly Pro His Ser Ala Leu Tyr
        275                 280                 285
Thr Met Met Lys Asp Gln Tyr Ala Asn Tyr Val Val Gln Lys Met Ile
    290                 295                 300
Asp Val Ala Glu Pro Gly Gln Arg Lys Ile Val Met His Lys Ile Arg
305                 310                 315                 320
Pro His Ile Ala Thr Leu Arg Lys Tyr Thr Tyr Gly Lys His Ile Leu
                325                 330                 335
Ala Lys Leu Glu Lys Tyr Tyr Met Lys Asn Gly Val Asp Leu Gly
            340                 345                 350

<210> SEQ ID NO 40
<211> LENGTH: 1863
<212> TYPE: DNA
<213> ORGANISM: Artificial Sequence
<220> FEATURE:
<223> OTHER INFORMATION: Recombinant

<400> SEQUENCE: 40
atggaattta gccaggatca gcatggtagc cgtttttattc agctgaagct tgaacgtgca      60
acaccggcag aacgtcagct ggtgtttaat gaaattctgc aagcagcata tcagctgatg     120
gttgatgtgt ttggcaacta cgtgatccag aaatttttg agtttggcag cctggaacag      180
aaactggcac tggcagaacg tatccgcggt catgttctga gcctggcact gcaaatgtat     240
ggttgtcgtg ttattcagaa agccctggaa ttcattccga cgatcagca gaatgaaatg      300
gttcgtgaac tggatggtca gtgctgaaa tgtgtgaaag atcagaatgg caatcatgtt      360
gtgcagaaat gcattgaatg tgttcagccg cagagcctgc aatttattat cgatgccttt     420
aaaggtcagg ttttttgcact gagcacccat ccgtacggtt gccgtgtgat ccagcgcatt     480
ctggaacatt gtctgccgga tcagaccctg ccgattctgg aagagctcca tcagcatata     540
atggaattt cccaagacca gcatgggtcc agattcattc agctgaaact ggagcgtgcc     600
acaccagctg agcgccagct tgtcttcaat gaaatcctcc aggctgccta ccaactcatg     660
gtggatgtgt ttggtaatta cgtcattcag aagttctttg aatttggcag tcttgaacag     720
aagctggctt tggcagaacg gattcgaggc cacgtcctgt cattggcact acagatgtat     780
ggctgccgtg ttatccagaa agctcttgag tttattcctt cagaccagca gaatgagatg     840
gttcgggaac tagatagcca tgtcttgaag tgtgtgaaag atcagaatgg caatcacgtg     900
gttcagaaat gcattgaatg tgtacagccc cagtctttgc aatttatcat cgatgcgttt     960
aagggacagg tatttgcctt atccacacat cctatggct gccgagtgat tcagagaatc    1020
ctggagcact gtctccctga ccagacactc cctattttag aggagcttca ccagcacaca    1080
```

```
gagcagctgg tacaggatca atatggaaat tatgtaatcc aacatgtact ggagcacggt   1140
cgtcctgagg ataaaagcaa aattgtagca gaaatccgag gcaatgtact tgtattgagt   1200
cagcacaaat ttgcaagcaa tgttgtggag aagtgtgtta ctcacgcctc acgtacggag   1260
cgcgctgtgc tcatcgatga ggtgtgcacc atgaacgacg tccccacag tgccttatac     1320 accatgatga aggaccagta tgccaactac gtggtccaga agatgattga cgtggcggag   1380
ccaggccagc ggaagatcgt catgcatgag ctccatcagc ataccgaaca gctggttcag   1440
gatcagtatg gaaactatgt gattcagcat gttctggaac atggtcgacc ggaagataaa   1500
agcaaaatcg tggccgaaat tcgtggtaat gtgctggttc tgagccagca taaatttgcc   1560
agcaacgtgg ttgaaaaatg tgttacccat gcaagccgta ccgaacgtgc agttctgatt   1620
gatgaagtgt gcaccatgaa tgatgggccc catagcgcac tgtataccat gatgaaagat   1680
cagtatgcga attacgtggt ccagaaaatg attgatgttg cagaaccggg tcagcgtaaa   1740
attgtgatgc ataaaatccg tccgcatatt gcaaccctgc gcaaatatac ctatggcaaa   1800
cacattctgg ccaaactgga aaatattat atgaaaaatg gcgtggacct gggcctcgag    1860
taa                                                                  1863
```

<210> SEQ ID NO 41
<211> LENGTH: 620
<212> TYPE: PRT
<213> ORGANISM: Artificial Sequence
<220> FEATURE:
<223> OTHER INFORMATION: Recombinant

<400> SEQUENCE: 41

```
Met Glu Phe Ser Gln Asp Gln His Gly Ser Arg Phe Ile Gln Leu Lys
1               5                   10                  15

Leu Glu Arg Ala Thr Pro Ala Glu Arg Gln Leu Val Phe Asn Glu Ile
            20                  25                  30

Leu Gln Ala Ala Tyr Gln Leu Met Val Asp Val Phe Gly Asn Tyr Val
        35                  40                  45

Ile Gln Lys Phe Phe Glu Phe Gly Ser Leu Glu Gln Lys Leu Ala Leu
    50                  55                  60

Ala Glu Arg Ile Arg Gly His Val Leu Ser Leu Ala Leu Gln Met Tyr
65                  70                  75                  80

Gly Cys Arg Val Ile Gln Lys Ala Leu Glu Phe Ile Pro Ser Asp Gln
                85                  90                  95

Gln Asn Glu Met Val Arg Glu Leu Asp Gly His Val Leu Lys Cys Val
            100                 105                 110

Lys Asp Gln Asn Gly Asn His Val Val Gln Lys Cys Ile Glu Cys Val
        115                 120                 125

Gln Pro Gln Ser Leu Gln Phe Ile Ile Asp Ala Phe Lys Gly Gln Val
    130                 135                 140

Phe Ala Leu Ser Thr His Pro Tyr Gly Cys Arg Val Ile Gln Arg Ile
145                 150                 155                 160

Leu Glu His Cys Leu Pro Asp Gln Thr Leu Pro Ile Leu Glu Glu Leu
                165                 170                 175

His Gln His Ile Met Glu Phe Ser Gln Asp Gln His Gly Ser Arg Phe
            180                 185                 190

Ile Gln Leu Lys Leu Glu Arg Ala Thr Pro Ala Glu Arg Gln Leu Val
        195                 200                 205

Phe Asn Glu Ile Leu Gln Ala Ala Tyr Gln Leu Met Val Asp Val Phe
```

```
            210                 215                 220
Gly Asn Tyr Val Ile Gln Lys Phe Phe Glu Phe Gly Ser Leu Glu Gln
225                 230                 235                 240

Lys Leu Ala Leu Ala Glu Arg Ile Arg Gly His Val Leu Ser Leu Ala
                245                 250                 255

Leu Gln Met Tyr Gly Cys Arg Val Ile Gln Lys Ala Leu Glu Phe Ile
                260                 265                 270

Pro Ser Asp Gln Gln Asn Glu Met Val Arg Glu Leu Asp Ser His Val
            275                 280                 285

Leu Lys Cys Val Lys Asp Gln Asn Gly Asn His Val Val Gln Lys Cys
        290                 295                 300

Ile Glu Cys Val Gln Pro Gln Ser Leu Gln Phe Ile Ile Asp Ala Phe
305                 310                 315                 320

Lys Gly Gln Val Phe Ala Leu Ser Thr His Pro Tyr Gly Cys Arg Val
                325                 330                 335

Ile Gln Arg Ile Leu Glu His Cys Leu Pro Asp Gln Thr Leu Pro Ile
                340                 345                 350

Leu Glu Glu Leu His Gln His Thr Glu Gln Leu Val Gln Asp Gln Tyr
                355                 360                 365

Gly Asn Tyr Val Ile Gln His Val Leu Glu His Gly Arg Pro Glu Asp
            370                 375                 380

Lys Ser Lys Ile Val Ala Glu Ile Arg Gly Asn Val Leu Val Leu Ser
385                 390                 395                 400

Gln His Lys Phe Ala Ser Asn Val Val Glu Lys Cys Val Thr His Ala
                405                 410                 415

Ser Arg Thr Glu Arg Ala Val Leu Ile Asp Glu Val Cys Thr Met Asn
                420                 425                 430

Asp Gly Pro His Ser Ala Leu Tyr Thr Met Met Lys Asp Gln Tyr Ala
            435                 440                 445

Asn Tyr Val Val Gln Lys Met Ile Asp Val Ala Glu Pro Gly Gln Arg
        450                 455                 460

Lys Ile Val Met His Glu Leu His Gln His Thr Glu Gln Leu Val Gln
465                 470                 475                 480

Asp Gln Tyr Gly Asn Tyr Val Ile Gln His Val Leu Glu His Gly Arg
                485                 490                 495

Pro Glu Asp Lys Ser Lys Ile Val Ala Glu Ile Arg Gly Asn Val Leu
            500                 505                 510

Val Leu Ser Gln His Lys Phe Ala Ser Asn Val Val Glu Lys Cys Val
        515                 520                 525

Thr His Ala Ser Arg Thr Glu Arg Ala Val Leu Ile Asp Glu Val Cys
530                 535                 540

Thr Met Asn Asp Gly Pro His Ser Ala Leu Tyr Thr Met Met Lys Asp
545                 550                 555                 560

Gln Tyr Ala Asn Tyr Val Val Gln Lys Met Ile Asp Val Ala Glu Pro
                565                 570                 575

Gly Gln Arg Lys Ile Val Met His Lys Ile Arg Pro His Ile Ala Thr
                580                 585                 590

Leu Arg Lys Tyr Thr Tyr Gly Lys His Ile Leu Ala Lys Leu Glu Lys
            595                 600                 605

Tyr Tyr Met Lys Asn Gly Val Asp Leu Gly Leu Glu
610                 615                 620

<210> SEQ ID NO 42
```

<210> SEQ ID NO 42
<211> LENGTH: 38
<212> TYPE: RNA
<213> ORGANISM: Artificial Sequence
<220> FEATURE:
<223> OTHER INFORMATION: Recombinant

<400> SEQUENCE: 42
ccggcuagca auuguauaua uuaauuuaau aaagcaug          38

<210> SEQ ID NO 43
<211> LENGTH: 38
<212> TYPE: RNA
<213> ORGANISM: Artificial Sequence
<220> FEATURE:
<223> OTHER INFORMATION: Recombinant

<400> SEQUENCE: 43
ccggcuagca auugaauaua uuaauuuaau aaagcaug          38

<210> SEQ ID NO 44
<211> LENGTH: 38
<212> TYPE: RNA
<213> ORGANISM: Artificial Sequence
<220> FEATURE:
<223> OTHER INFORMATION: Recombinant

<400> SEQUENCE: 44
ccggcuagca auugcauaua uuaauuuaau aaagcaug          38

<210> SEQ ID NO 45
<211> LENGTH: 38
<212> TYPE: RNA
<213> ORGANISM: Artificial Sequence
<220> FEATURE:
<223> OTHER INFORMATION: Recombinant

<400> SEQUENCE: 45
ccggcuagca auuggauaua uuaauuuaau aaagcaug          38

<210> SEQ ID NO 46
<211> LENGTH: 10
<212> TYPE: RNA
<213> ORGANISM: Artificial Sequence
<220> FEATURE:
<223> OTHER INFORMATION: Recombinant

<400> SEQUENCE: 46
auuguauaua          10

<210> SEQ ID NO 47
<211> LENGTH: 10
<212> TYPE: RNA
<213> ORGANISM: Artificial Sequence
<220> FEATURE:
<223> OTHER INFORMATION: Recombinant

<400> SEQUENCE: 47
auugcauaua          10

<210> SEQ ID NO 48
<211> LENGTH: 38
<212> TYPE: RNA
<213> ORGANISM: Artificial Sequence
<220> FEATURE:
<223> OTHER INFORMATION: Recombinant

<400> SEQUENCE: 48

-continued ccggcuagca aucguauaua uuaauuuaau aaagcaug        38

<210> SEQ ID NO 49
<211> LENGTH: 38
<212> TYPE: RNA
<213> ORGANISM: Artificial Sequence
<220> FEATURE:
<223> OTHER INFORMATION: Recombinant

<400> SEQUENCE: 49
ccggcuagca auucuauaua uuaauuuaau aaagcaug        38

<210> SEQ ID NO 50
<211> LENGTH: 38
<212> TYPE: RNA
<213> ORGANISM: Artificial Sequence
<220> FEATURE:
<223> OTHER INFORMATION: Recombinant

<400> SEQUENCE: 50
ccggcuagca auugucuaua uuaauuuaau aaagcaug        38

<210> SEQ ID NO 51
<211> LENGTH: 38
<212> TYPE: RNA
<213> ORGANISM: Artificial Sequence
<220> FEATURE:
<223> OTHER INFORMATION: Recombinant

<400> SEQUENCE: 51
ccggcuagca auuguacaua uuaauuuaau aaagcaug        38

<210> SEQ ID NO 52
<211> LENGTH: 38
<212> TYPE: RNA
<213> ORGANISM: Artificial Sequence
<220> FEATURE:
<223> OTHER INFORMATION: Recombinant

<400> SEQUENCE: 52
ccggcuagca auuguaucua uuaauuuaau aaagcaug        38

<210> SEQ ID NO 53
<211> LENGTH: 38
<212> TYPE: RNA
<213> ORGANISM: Artificial Sequence
<220> FEATURE:
<223> OTHER INFORMATION: Recombinant

<400> SEQUENCE: 53
ccggcuagca auuguauaca uuaauuuaau aaagcaug        38

<210> SEQ ID NO 54
<211> LENGTH: 38
<212> TYPE: RNA
<213> ORGANISM: Artificial Sequence
<220> FEATURE:
<223> OTHER INFORMATION: Recombinant

<400> SEQUENCE: 54
ccggcuagca auuguauauc uuaauuuaau aaagcaug        38

<210> SEQ ID NO 55
<211> LENGTH: 38
<212> TYPE: RNA

```
<213> ORGANISM: Artificial Sequence
<220> FEATURE:
<223> OTHER INFORMATION: Recombinant

<400> SEQUENCE: 55
ccggcuagca auuguauaua uuaauauaau aaagcaug                              38

<210> SEQ ID NO 56
<211> LENGTH: 38
<212> TYPE: RNA
<213> ORGANISM: Artificial Sequence
<220> FEATURE:
<223> OTHER INFORMATION: Recombinant

<400> SEQUENCE: 56
ccggcuagca auuguauaua uuaauauauu aaagcaug                              38

<210> SEQ ID NO 57
<211> LENGTH: 38
<212> TYPE: RNA
<213> ORGANISM: Artificial Sequence
<220> FEATURE:
<223> OTHER INFORMATION: Recombinant

<400> SEQUENCE: 57
ccggcuagca auuguauaua uuaauauaua aaagcaug                              38

<210> SEQ ID NO 58
<211> LENGTH: 38
<212> TYPE: RNA
<213> ORGANISM: Artificial Sequence
<220> FEATURE:
<223> OTHER INFORMATION: Recombinant

<400> SEQUENCE: 58
ccggcuagca auuguauaua uuaauauaua caagcaug                              38

<210> SEQ ID NO 59
<211> LENGTH: 46
<212> TYPE: RNA
<213> ORGANISM: Artificial Sequence
<220> FEATURE:
<223> OTHER INFORMATION: Recombinant

<400> SEQUENCE: 59
ccggcuagca auuguuguau auaauauauu aauuuaauaa agcaug                     46

<210> SEQ ID NO 60
<211> LENGTH: 46
<212> TYPE: RNA
<213> ORGANISM: Artificial Sequence
<220> FEATURE:
<223> OTHER INFORMATION: Recombinant

<400> SEQUENCE: 60
ccggcuagca aucccuguau auaauauauu aauuuaauaa agcaug                     46

<210> SEQ ID NO 61
<211> LENGTH: 46
<212> TYPE: RNA
<213> ORGANISM: Artificial Sequence
<220> FEATURE:
<223> OTHER INFORMATION: Recombinant

<400> SEQUENCE: 61
ccggcuagca auugucccccu auaauauauu aauuuaauaa agcaug                    46
```

```
<210> SEQ ID NO 62
<211> LENGTH: 10
<212> TYPE: PRT
<213> ORGANISM: Artificial Sequence
<220> FEATURE:
<223> OTHER INFORMATION: Recombinant

<400> SEQUENCE: 62

Gln Tyr Gly Cys Tyr Val Ile Arg His Val
1               5                   10
```

PEPTIDES FOR THE SPECIFIC BINDING OF RNA TARGETS

CROSS-REFERENCE TO RELATED APPLICATION

This application is the U.S. national phase of PCT Application No. PCT/AU2011/001519 filed on Nov. 24, 2011, which claims priority to Australian Patent Application No. 2010905192 filed on Nov. 24, 2010, the disclosures of which are incorporated in their entirety by reference herein.

SEQUENCE LISTING

The text file is Sequence_Listing_3.txt, created on Feb. 22, 2016, filed herewith and of size 74 KB, is hereby incorporated by reference.

TECHNICAL FIELD

This invention broadly relates to recombinant polypeptides comprising a RNA-binding domain capable of specifically binding to a desired RNA target molecule. The invention also relates to fusion proteins comprising the recombinant polypeptides and an effector domain; to isolated nucleic acids encoding same as well as recombinant vectors and host cells comprising nucleic acids encoding same; to compositions comprising the recombinant polypeptides or fusion proteins and use thereof; as well as methods of regulating expression of a gene and systems and kits for use therefor.

BACKGROUND ART

The following discussion of the background art is intended to facilitate an understanding of the present invention only. The discussion is not an acknowledgement or admission that any of the material referred to is or was part of the common general knowledge as at the priority date of the application.

The regulation of gene expression and cellular function in cells is controlled at many levels, including the regulation of the extent of chromatin structure, epigenetic control, transcriptional initiation and control of the rate thereof, messenger RNA (mRNA) transcript processing and modification, mRNA transport, mRNA transcript stability, translational initiation, control of transcript levels by small non-coding RNAs, post-translational modification, protein transport, and control of protein stability.

Antisense RNA (aRNA) and RNA interference (RNAi) technologies are well established tools for regulating gene expression through steric hindrance of translation and mRNA transcript degradation respectively. RNAi involves the introduction of short interfering RNA (siRNA) or microRNA (miRNA) into a cell, followed by the activation of RNAi cellular machinery and cleavage of a target messenger RNA (mRNA) transcript by RNA-induced silencing complex (RISC). However, the design of functional siRNA that is appropriately recognised by RNAi cellular machinery is highly complex and subject to various constraints (Tuschl, T. et al. (1999) Genes & Dev 13: 3191-3197). The siRNA must be 19-21 nucleotides in length and have a 2-nt 3' overhang. The siRNA must exhibit limited G/C content and avoid consecutive stretches of the same base. Furthermore, the selectivity of strand loading into the RISC complex depends on the differential thermodynamic stabilities of the two ends of an siRNA duplex (Schwarz, S. D. et al. (2003) Cell 115:199-208), the less thermodynamically stable end being favoured for binding.

The design of pre-miRNA or miRNA to be processed into siRNA is further complicated by the requirement of secondary structural elements such as imperfectly base-paired stem regions flanked by free 5' and 3' ends and an unpaired loop region (Lund, E. and Dahlberg, J. E. (2006) Regulatory RNAs, Volume 71 of Cold Spring Harbor symposia on quantitative biology, CSHL Press). Thus, the constraints within which siRNA and miRNA molecules must be designed not only make the production of these molecules both challenging and complex but also limit the number and sequence of potential mRNA targets.

Despite the purported specificity of RNAi and aRNA technology for specific mRNA targets, cross-hybridization and non-specific binding can occur. In addition to the possibility for cross-hybridization of the antisense strand of siRNA to different mRNAs, siRNAs have demonstrated undesirable binding to various proteins (Bruckner, I. & Tremblay, G. A. (2000) Biochemistry 39: 11463-11466) causing significant nonspecific effects (Stein, C. A. (1995) Nat Med 1: 1119-1121). Moreover, the binding to affinity of siRNA-mediated binding of activated RISC to target mRNA (RNA-RNA interaction) is limited to that provided by canonical Watson and Crick base pairing, with guanine-cytosine interactions restricted to the expected three intermolecular hydrogen bonds, and adenine-uracil or uracil-guanine to the expected two intermolecular hydrogen bonds. Further disadvantages of RNAi technology include the need for transfection reagents or delivery vehicles, low and variable transfection efficiency sometimes necessitating the use of multiple transfection steps, partial and transient gene suppression effects, dependence upon processing by RNAi machinery, the limitation of mechanism to mRNA transcript degradation, and undesirable siRNA hairpin formation. siRNA is also known to be a potent activator of the mammalian innate immune system or IFN response (Judge, A, et al. (2008) Human Gene Therapy. (2008) 19: 111-124). The use of siRNA has been reported to cause an undesirable stimulation of immune activity and inflammatory response which may be further potentiated by the use of delivery vehicles, resulting in significant side effects due to excessive cytokine release and associated inflammatory syndromes. The potential for siRNA-based drugs to be rendered immunogenic is thus a cause for concern and has implications for both the development of siRNA-based drugs and the interpretation of gene-silencing effects elicited by siRNA (Judge, supra).

Alternatives to RNAi include the use of naturally occurring RNA-binding proteins which have been found to play essential roles in the regulation of gene expression. However, the modes by which such proteins bind RNA are idiosyncratic, restricted to sequence specific interactions, and difficult to predict so that their general use in biotechnological and medical applications is restricted. Information on the physiological targets of many RNA-proteins is limited and the binding of most RNA-proteins to their targets is reported to be idiosyncratic or require a combination of sequence and structural features such that their binding cannot be generally applied to other targets.

The PUF family of proteins (*Drosophila Pumilio* (Pum) and *C. elegans* FBF (fem-3 binding factor)) are an evolutionarily conserved family of RNA-binding proteins including *Drosophila Pumilio* and *Caenorhabditis elegans* FBF (for a review see Spassov, D. S. & Jurecic, R. (2003) IUBMB Life, 55: 359-366). PUF proteins contain an RNA-binding domain, known as the PUF domain or the *Pumilio* homology domain (PUM-HD), typically composed of eight tandem imperfect repeats of 36 amino acids plus conserved N and C-terminal flanking regions, aligned in tandem to form an extended curved arc-like molecule (Edwards, T. A. et al. (2001) Cell 105: 281-289). Target RNA binds to the inner concave surface of the protein, each of the eight repeats contacting a separate RNA base via three conserved amino acid residues positioned in the middle of the repeats (Wang, X. et al. (2002) Cell 110: 501-512). PUF proteins regulate RNA stability and translation by binding to specific sequences, such as the nanos response element (NRE), that are most often found in 3' untranslated regions of target mRNAs (Gupta, supra). The PUM 1 NRE sequence is composed only of adenine, guanine or uracil.

The modular nature of the PUF-RNA interaction has been used to rationally engineer the binding specificity of PUF domains (Cheong, C. G. & Hall, T. M. (2006) PNAS 103: 13635-13639; Wang, X. et al (2002) Cell 110: 501-512). However, only the successful design of PUF domains with repeats that recognize adenine, guanine or uracil have been reported to date (Cheong, supra; Wang, supra). The specificity of individual repeats recognizing adenine, guanine or uracil were respectively switched by mutating only the positions that make contacts with the Watson-Crick edge of the base, providing engineered PUF domains capable of recognising endogenous RNA sequences composed of adenine, guanine or uracil (Wang, Y. Et al (2009) Nat Methods 6: 825-830; Tilsner, J. et al (2009) Plant 57: 758-770; Ozawa, T. et al (2007) Nat Methods 4: 413-419). Most of the known naturally occurring target sequences of PUM1, such as the NRE sequence, are composed of only adenine, guanine or uracil. However, despite focussed attempts to engineer PUF domains, the use of PUF domains designed with repeats that recognize these bases has remained substantially limited to sequences composed only of adenine, guanine or uracil.

There thus exists is a continued need for alternative methods for the specific regulation of gene expression and for agents for use therefor.

SUMMARY OF INVENTION

According to the invention there is provided a recombinant polypeptide comprising at least one PUF RNA-binding domain capable of specifically binding to a cytosine RNA base.

Further features of the invention provide for the PUF RNA-binding domain to comprise at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K);

$X_2$ is selected from the group including histidine (H), phenylalanine (F), tyrosine (Y), and asparagine (N);

$X_3$ is selected from the group including glycine (G) and alanine (A);

$X_4$ is selected from the group including glycine (G), alanine (A), serine (S), threonine (T) and cysteine (C);

$X_5$ is selected from the group including arginine (R), tyrosine (Y), histidine (H), and asparagine (N);

$X_6$ is selected from the group including phenylalanine (F), leucine (L), and valine (V);

$X_7$ is selected from the group including isoleucine (I), leucine (L), and valine (V);

$X_8$ is arginine (R);

$X_9$ is selected from the group including leucine (L), lysine (K), arginine (R), glutamine (Q), and histidine (H);

$X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V);

and wherein the RNA base-binding motif is operably capable of specifically binding to a cytosine RNA base.

In one embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is glutamine (Q); $X_2$ is tyrosine (Y); $X_3$ is glycine (G); $X_4$ is selected from the group including glycine (G), alanine (A), serine (S), threonine (T) and cysteine (C); $X_5$ is tyrosine (Y); $X_6$ is valine (V); $X_7$ is isoleucine (I); $X_8$ is arginine (R); $X_9$ is histidine (H); $X_{10}$ is valine (V); and $X_{11}$ is leucine (L).

In a preferred embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is glutamine (Q); $X_2$ is tyrosine (Y); $X_3$ is glycine (G); $X_4$ is glycine (G); $X_5$ is tyrosine (Y); $X_6$ is valine (V); $X_7$ is isoleucine (I); $X_8$ is arginine (R); $X_9$ is histidine (H); $X_{10}$ is valine (V); and $X_{11}$ is leucine (L).

In another preferred embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is glutamine (Q); $X_2$ is tyrosine (Y); $X_3$ is glycine (G); $X_4$ is alanine (A); $X_5$ is tyrosine (Y); $X_6$ is valine (V); $X_7$ is isoleucine (I); $X_8$ is arginine (R); $X_9$ is histidine (H); $X_{10}$ is valine (V); and $X_{11}$ is leucine (L).

In another preferred embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is glutamine (Q); $X_2$ is tyrosine (Y); $X_3$ is glycine (G); $X_4$ is serine (S); $X_5$ is tyrosine (Y); $X_6$ is valine (V); $X_7$ is isoleucine (I); $X_8$ is arginine (R); $X_9$ is histidine (H); $X_{10}$ is valine (V); and $X_{11}$ is leucine (L).

In another preferred embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is glutamine (Q); $X_2$ is tyrosine (Y); $X_3$ is glycine (G); $X_4$ is threonine (T); $X_5$ is tyrosine (Y); $X_6$ is valine (V); $X_7$ is isoleucine (I); $X_8$ is arginine (R); $X_9$ is histidine (H); $X_{10}$ is valine (V); and $X_{11}$ is leucine (L).

In another preferred embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is glutamine (Q); $X_2$ is tyrosine (Y); $X_3$ is glycine (G); $X_4$ is cysteine (C); $X_5$ is tyrosine (Y); $X_6$ is valine (V); $X_7$ is isoleucine (I); $X_8$ is arginine (R); $X_9$ is histidine (H); $X_{10}$ is valine (V); and $X_{11}$ is leucine (L).

Alternatively, the PUF RNA-binding domain may comprise at least one RNA base-binding motif of the general formula QYGXYVIRHVL wherein X is an amino acid with a small or nucleophilic side chain.

In an embodiment of the invention, the PUF RNA-binding domain comprises at least one RNA base-binding motif of the general formula QYGXYVIRHVL wherein X is an amino acid selected from the group comprising glycine (G), alanine (A), serine (S), threonine (T), and cysteine (C).

Further features of the invention provide for the PUF RNA-binding domain to comprise a plurality of RNA base-binding motifs, at least one of which is capable of specifically binding to a cytosine RNA base; and further for the plurality of RNA base-binding motifs to comprise a first RNA base-binding motif capable of specifically binding to a cytosine RNA base and a second RNA base-binding motif capable of specifically binding to an RNA base comprising one of adenosine, guanine, or uracil, wherein the first and second RNA base-binding motifs are synergistically operable to specifically bind the RNA bases.

In another embodiment of the invention, the PUF RNA-binding domain comprises a plurality of consecutively ordered RNA base-binding motifs synergistically operable to bind a target RNA molecule with a target RNA sequence, each RNA base-binding motif capable of specifically binding to a cytosine, adenosine, guanine, or uracil RNA base, wherein the consecutive order of the RNA base-binding motifs corresponds with the consecutive order of the RNA bases in the target RNA sequence.

In a preferred embodiment of the invention, the plurality of consecutively ordered RNA base-binding motifs comprises at least one first RNA base-binding motif having a sequence of any one of SEQ ID NOS: 1-5 and at least one second RNA base-binding motif having a sequence of any one of SEQ ID NOS: 6-13.

Further features of the invention provide for the plurality of RNA base-binding motifs to comprise between 2 and 40 RNA base-binding motifs. Preferably, the plurality of RNA base-binding motifs comprise between 8 and 16 RNA base-binding motifs.

In a preferred embodiment of the invention, the recombinant polypeptide has a sequence of any one of SEQ ID NOS: 14-18 or any one of SEQ ID NOS: 24-30 or SEQ ID NO: 41.

In a more preferred embodiment of the invention, the recombinant polypeptide has a sequence of any one of SEQ ID NOS: 14-18.

In a further preferred embodiment of the invention, the recombinant polypeptide has a sequence of any one of SEQ ID NOS: 24-30.

In a further preferred embodiment of the invention, the recombinant polypeptide has a sequence of SEQ ID NO: 41.

In a further preferred embodiment of the invention, the amino acid spacers are derived from SEQ ID NO 39, or part thereof.

The invention also provides a fusion protein comprising at least one PUF RNA-binding domain capable of specifically binding to a cytosine RNA base, and an effector domain.

In an embodiment of the invention, the PUF RNA-binding domain of the fusion protein comprises a plurality of consecutively ordered RNA base-binding motifs synergistically operable to bind a target RNA molecule with a target RNA sequence, each RNA base-binding motif capable of specifically binding to a cytosine, adenosine, guanine, or uracil RNA base, wherein the consecutive order of the RNA base-binding motifs corresponds with the consecutive order of the RNA bases in the target RNA sequence.

In a preferred embodiment of the invention the plurality of consecutively ordered RNA base-binding motifs of the PUF RNA-binding domain of the fusion protein comprises at least one first RNA base-binding motif having a sequence of any one of SEQ ID NOS: 1-5 and at least one second RNA base-binding motif having a sequence of any one of SEQ ID NOS: 6-13.

The invention further provides for an isolated nucleic acid encoding the recombinant polypeptide or the fusion protein of the invention.

The isolated nucleic acid may have a sequence selected from the group comprising any one of SEQ ID NOS: 19-23, any one of SEQ ID NOS: 31-37, SEQ ID NO: 40, and a sequence at least 80% homologous to any one of SEQ ID NOS: 19-23 and 31-37.

In a preferred embodiment of the invention, the isolated nucleic acid has a sequence selected from the group comprising any one of SEQ ID NOS: 19-23.

In another preferred embodiment of the invention, the isolated nucleic acid has a sequence selected from the group comprising any one of SEQ ID NOS: 31-37.

In a further preferred embodiment of the invention, the isolated nucleic acid has a sequence of SEQ ID NO: 40.

The invention yet further provides a recombinant vector comprising nucleic acid encoding the recombinant polypeptide or the fusion protein of the invention.

The invention extends to host cells comprising nucleic acid encoding the recombinant polypeptide or the fusion protein of the invention; and for the nucleic acid of the host cell to have a sequence selected from the group comprising any one of SEQ ID NOS: 19-23, any one of SEQ ID NOS: 31-37, SEQ ID NO: 40, and a sequence at least 80% homologous to any one of SEQ ID NOS: 19-23 and 31-37.

The host cells may be selected from a wide variety of suitable host cells, including prokaryotic and eukaryotic cells, and may be selected according to the chosen expression system such as bacterial, yeast, insect or mammalian expression systems. Regulating sequences for gene expression in the various expression systems may be also be included in the host cells for. By way of illustration, the nucleic acids of the preferred embodiments of the invention are adapted for yeast host cells, preferably *Saccharomyces cerevisiae*, more preferably *Saccharomyces cerevisiae* YBZ-1. However, it is understood that the scope of the invention is not limited thereby.

The invention also provides for a composition comprising the recombinant polypeptide of the invention or the fusion protein of the invention or the isolated nucleic acid of the invention or the recombinant vector of the invention.

The invention extends to the use of an effective amount of the recombinant polypeptide of the invention or the fusion protein of the invention or the isolated nucleic acid of the invention or the recombinant vector of the invention in the manufacture of a medicament for regulating gene expression.

The invention further provides for a method of regulating expression of a gene in a cell, the method comprising the step of introducing into the cell a recombinant polypeptide comprising a PUF RNA-binding domain comprising a plurality of consecutively ordered RNA base-binding motifs synergistically operable to bind a target RNA molecule with a target RNA sequence, each RNA base-binding motif capable of specifically binding to a cytosine, adenosine, guanine, or uracil RNA base, wherein the consecutive order of the RNA base-binding motifs corresponds with the consecutive order of the RNA bases in the target RNA sequence; wherein the specific binding of the recombinant polypeptide to the target RNA alters the expression of the gene.

The invention further provides for a pharmaceutical composition comprising the recombinant polypeptide of the invention or the fusion protein of the invention or the isolated nucleic acid of the invention or the recombinant vector of the invention.

The invention also provides a system for regulating gene expression comprising
(a) a modular set of isolated nucleic acids encoding a plurality of RNA base-binding motifs, the set including: at least one isolated nucleic acid encoding a RNA base-binding motif capable of specifically binding to a cytosine RNA base and at least one isolated nucleic acid encoding a RNA base-binding motif capable of specifically binding to an adenosine RNA base or a guanine RNA base or a uracil RNA base;
(b) means for annealing the isolated nucleic acids of the modular set in a desired sequence to produce an isolated nucleic acid encoding an expressable recombinant polypeptide comprising a PUF RNA-binding domain having a plurality of consecutively ordered RNA base-binding motifs; and
(c) a target RNA molecule with a target RNA sequence, wherein the consecutive order of the RNA base-binding motifs corresponds with the consecutive order of the RNA bases in the target RNA sequence The invention extends to a kit for regulating gene expression comprising
(a) a modular set of isolated nucleic acids encoding a plurality of RNA base-binding motifs, the set including: at least one isolated nucleic acid encoding a RNA base-binding motif capable of specifically binding to a cytosine RNA base and at least one isolated nucleic acid encoding a RNA base-binding motif capable of specifically binding to an adenosine RNA base or a guanine RNA base or a uracil RNA base;
(b) means for annealing the isolated nucleic acids of the modular set in a desired sequence to produce an isolated nucleic acid encoding a recombinant polypeptide comprising a PUF RNA-binding domain having a plurality of consecutively ordered RNA base-binding motifs; and
(c) optionally, a target RNA molecule with a target RNA sequence, wherein the consecutive order of the RNA base-binding motifs corresponds with the consecutive order of the RNA bases in the target RNA sequence In a preferred embodiment of the invention, the plurality of consecutively ordered RNA base-binding motifs comprises at least one first RNA base-binding motif having a sequence of any one of SEQ ID NOS: 1-5 and at least one second RNA base-binding motif having a sequence of any one of SEQ ID NOS: 6-12.

Further features of the invention provide for the plurality of RNA base-binding motifs to comprise between 8 and 21 RNA base-binding motifs.

In a preferred embodiment of the invention, the recombinant polypeptide comprises eight operably linked RNA base-binding motifs comprising in consecutive order the amino acid sequences of SEQ ID NO: 6, SEQ ID NO: 7, SEQ ID NO: 8, SEQ ID NO: 9, SEQ ID NO: 10, any one of SEQ ID NOS: 1-5, SEQ ID NO 11, and SEQ ID NO 12.

In another preferred embodiment of the invention, the recombinant polypeptide has a sequence of any one of SEQ ID NOS: 13-17.

In a further preferred embodiment of the invention, the amino acid spacers are derived from SEQ ID NO 23 or SEQ ID NO 24, or part thereof.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which:

FIG. 7 shows the amino acid sequences of the GR, AR, SR, TR, and CR recombinant proteins of the invention in which the PUF domain repeats are internally aligned, showing amino acids at positions 12 and 16 of each PUF domain repeat as underlined, and engineered amino acids at positions 12 and 16 of each PUF domain repeat 6 as underlined and in bold. The sequences from top to bottom are SEQ ID NO: 14, SEQ ID NO: 15; SEQ ID NO: 16, SEQ ID NO: 17, and SEQ ID NO: 18.

Figure 1:
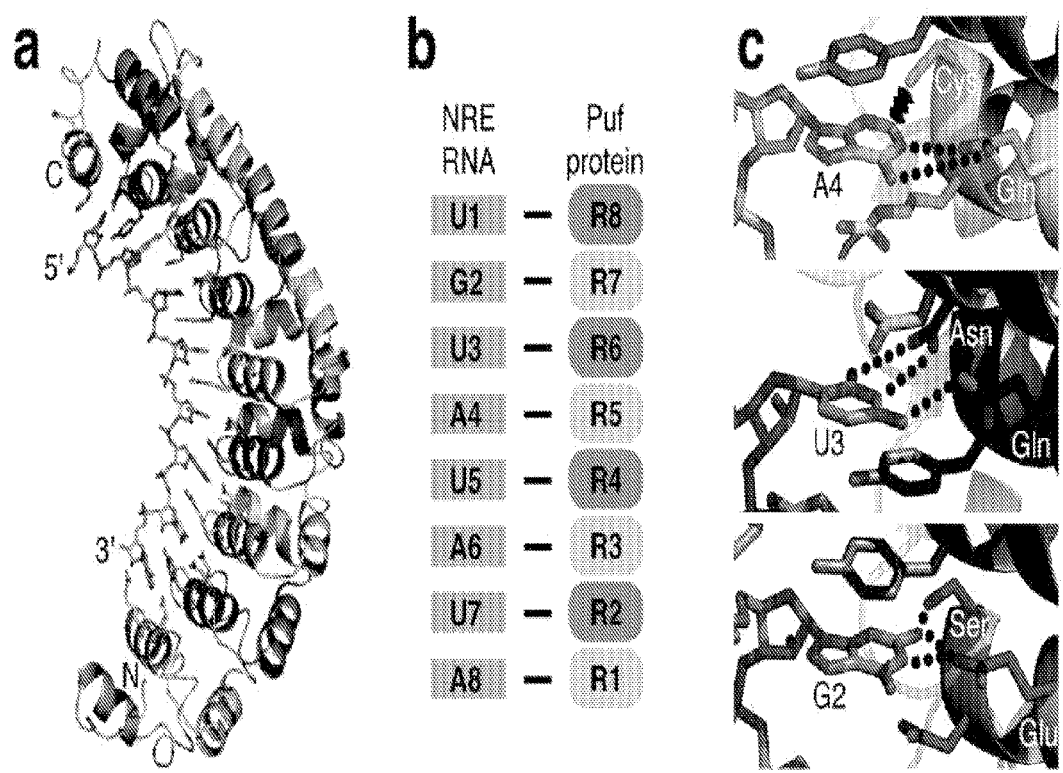
FIG. 1 shows (a) a ribbon representation of the tertiary protein structure of the human PUM1 PUF domain in complex with RNA, (b) a schematic representation of the recognition of RNA bases in the NRE RNA by the PUF repeats of PUM1, and (c) a close up view of the side-chain interactions of adenine (upper panel), uracil (middle panel) and guanine (lower panel) of the RNA target and the human PUM1 PUF domain shown in FIG. 1 illustrating how individual repeats bind adenine, guanine and uracil.

SEQ ID NO 1 is the amino acid sequence of the GR repeat of Example 1;
SEQ ID NO 2 is the amino acid sequence of the AR repeat of Example 1;
SEQ ID NO 3 is the amino acid sequence of the SR repeat of Example 1;
SEQ ID NO 4 is the amino acid sequence of the TR repeat of Example 1;
SEQ ID NO 5 is the amino acid sequence of the CR repeat of Example 1;
SEQ ID NO 6 is the amino acid sequence of repeat 1 of wild type human PUM1;
SEQ ID NO 7 is the amino acid sequence of repeat 2 of wild type human PUM1;
SEQ ID NO 8 is the amino acid sequence of repeat 3 of wild type human PUM1;
SEQ ID NO 9 is the amino acid sequence of repeat 4 of wild type human PUM1;
SEQ ID NO 10 is the amino acid sequence of repeat 5 of wild type human PUM1;
SEQ ID NO 11 is the amino acid sequence of repeat 6 of wild type human PUM1;
SEQ ID NO 12 is the amino acid sequence of repeat 7 of wild type human PUM1;
SEQ ID NO 13 is the amino acid sequence of repeat 8 of wild type human PUM1;
SEQ ID NO 14 is the amino acid sequence of the GR protein of Example 1 and of the GR protein-repeat 6 of Example 2;
SEQ ID NO 15 is the amino acid sequence of the AR protein of Example 1;
SEQ ID NO 16 is the amino acid sequence of the SR protein of Example 1;
SEQ ID NO 17 is the amino acid sequence of the TR protein of Example 1;
SEQ ID NO 18 is the amino acid sequence of the CR protein of Example 1;
SEQ ID NO 19 is the DNA sequence encoding the GR protein of Example 1 and the GR protein-repeat 6 of Example 2;
SEQ ID NO 20 is the DNA sequence encoding the AR protein of Example 1;
SEQ ID NO 21 is the DNA sequence encoding the SR protein of Example 1;
SEQ ID NO 22 is the DNA sequence encoding the TR protein of Example 1;
SEQ ID NO 23 is the DNA sequence encoding the CR protein of Example 1;
SEQ ID NO 24 is the amino acid sequence of the GR protein—repeat 1 of Example 2;
SEQ ID NO 25 is the amino acid sequence of the GR protein—repeat 2 of Example 2;
SEQ ID NO 26 is the amino acid sequence of the GR protein—repeat 3 of Example 2;
SEQ ID NO 27 is the amino acid sequence of the GR protein—repeat 4 of Example 2;
SEQ ID NO 28 is the amino acid sequence of the GR protein—repeat 5 of Example 2;
SEQ ID NO 29 is the amino acid sequence of the GR protein—repeat 7 of Example 2;
SEQ ID NO 30 is the amino acid sequence of the GR protein—repeat 8 of Example 2;
SEQ ID NO 31 is the DNA sequence encoding the GR protein—repeat 1 of Example 2;
SEQ ID NO 32 is the DNA sequence encoding the GR protein—repeat 2 of Example 2;
SEQ ID NO 33 is the DNA sequence encoding the GR protein—repeat 3 of Example 2;
SEQ ID NO 34 is the DNA sequence encoding the GR protein—repeat 4 of Example 2;
SEQ ID NO 35 is the DNA sequence encoding the GR protein—repeat 5 of Example 2;
SEQ ID NO 36 is the DNA sequence encoding the GR protein—repeat 7 of Example 2;
SEQ ID NO 37 is the DNA sequence encoding the GR protein—repeat 8 of Example 2;
SEQ ID NO 38 is the cDNA sequence from human PUM1, NM_014676, that encodes the Puf domain; and
SEQ ID NO 39 is the amino acid sequence of the Puf domain from human PUM1, amino acids 828 to 1176.
SEQ ID NO 40 is the DNA sequence encoding PUF×2, the 16 repeat PUF protein, of Example 3;
SEQ ID NO 41 is the amino acid sequence of PUF×2, the 16 repeat PUF protein;
SEQ ID NO 42 is the RNA sequence to which the NRE primer corresponds;
SEQ ID NO 43 is the RNA sequence to which the NREU3A primer corresponds;
SEQ ID NO 44 is the RNA sequence to which the NREU3C primer corresponds;
SEQ ID NO 45 is the RNA sequence to which the NREU3G primer corresponds;
SEQ ID NO 46 is the RNA sequence to which the NRE (FI) primer corresponds;
SEQ ID NO 47 is the RNA sequence to which the NREU3C (FI) primer corresponds;

SEQ ID NO 48 is the RNA sequence to which the NREU1C primer corresponds;

SEQ ID NO 49 is the RNA sequence to which the NREG2C primer corresponds;

SEQ ID NO 50 is the RNA sequence to which the NREA4C primer corresponds;

SEQ ID NO 51 is the RNA sequence to which the NREU5C primer corresponds;

SEQ ID NO 52 is the RNA sequence to which the NREA6C primer corresponds;

SEQ ID NO 53 is the RNA sequence to which the NREU7C primer corresponds;

SEQ ID NO 54 is the RNA sequence to which the NREA8C primer corresponds;

SEQ ID NO 55 is the RNA sequence to which the NREstem5 primer corresponds;

SEQ ID NO 56 is the RNA sequence to which the NREstem6 primer corresponds;

SEQ ID NO 57 is the RNA sequence to which the NREstem7 primer corresponds;

SEQ ID NO 58 is the RNA sequence to which the NREstem8 primer corresponds;

SEQ ID NO 59 is the RNA sequence to which the NREx2 primer corresponds;

SEQ ID NO 60 is the RNA sequence to which the NREx2mut1 primer corresponds; and

SEQ ID NO 61 is the RNA sequence to which the NREx2mut2 primer corresponds.

DESCRIPTION OF EMBODIMENTS

Throughout this specification, unless the context requires otherwise, the word "comprise" or variations such as "comprises" or "comprising", will be understood to imply the inclusion of a stated integer or group of integers but not the exclusion of any other integer or group of integers General Standard techniques may be used for recombinant DNA molecule, and protein production, as well as for tissue culture and cell transformation. Protein purification techniques are typically performed according to the manufacturer's specifications or as commonly accomplished in the art using conventional procedures such as those set forth in Sambrook et al. (Molecular Cloning: A Laboratory Manual. Cold Spring Harbor Laboratory Press, Cold Spring Harbor, N.Y. [1989]), or as described herein. Unless specific definitions are provided, the nomenclature used in connection with, and the laboratory procedures and techniques of molecular biology and biochemistry described herein, are those well known and commonly used in the art.

Throughout the specification, unless the context requires otherwise, the word "comprise" or variations such as "comprises" or "comprising", will be understood to imply the inclusion of a stated integer or group of integers but not the exclusion of any other integer or group of integers.

Each document, reference, patent application or patent cited in this text is expressly incorporated herein in their entirely by reference, which means that it should be read and considered by the reader as part of this text. That the document, reference, patent application, or patent cited in this text is not repeated in this text is merely for reasons of conciseness.

Reference to cited material or information contained in the text should not be understood as a concession that the material or information was part of the common general knowledge or was known in Australia or any other country.

Those skilled in the art will appreciate that the invention described herein is susceptible to variations and modifications other than those specifically described. It is to be understood that the invention includes all such variation and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

Detailed Description of the Embodiments of the Invention

A recombinant polypeptide is provided comprising at least one PUF RNA-binding domain capable of specifically binding to a cytosine RNA base.

The PUF RNA-binding domain of the recombinant polypeptide may comprise at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In an embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is glutamine (Q); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is valine (V); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is methionine (M); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is proline (P); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is glutamic acid (E); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is histidine (H); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is phenylalanine (F); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is tyrosine (Y); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is glycine (G); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is glycine (G); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is alanine (A); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is serine (S); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is threonine (T); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is arginine (R); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is tyrosine (Y); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is histidine (H); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is phenylalanine (F); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is leucine (L); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is isoleucine (I); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is leucine (L); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is leucine (L); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is lysine (K); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is arginine (R); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is glutamine (Q); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is histidine (H); $X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is lysine (K); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is phenylalanine (F); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is alanine (A); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is cysteine (C); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is isoleucine (I); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is valine (V); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is leucine (L); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is methionine (M); and $X_{11}$ is selected from the group including leucine (L), phenylalanine (F), isoleucine (I), and valine (V); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is leucine (L); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is phenylalanine (F); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is isoleucine (I); and wherein the RNA base-binding motif is operably capable of specifically binding to a cytosine RNA base.

In another embodiment of the invention, the PUF RNA-binding domain comprises at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K); $X_2$ is selected from the group including histidine (H), phenylalanine (F), tyrosine (Y), and asparagine (N); $X_3$ is selected from the group including glycine (G) and alanine (A); $X_4$ is selected from the group including glycine (G), alanine (A), serine (S), threonine (T) and cysteine (C); $X_5$ is selected from the group including arginine (R), tyrosine (Y), histidine (H), and asparagine (N); $X_6$ is selected from the group including phenylalanine (F), leucine (L), and valine (V); $X_7$ is selected from the group including isoleucine (I), leucine (L), and valine (V); $X_8$ is arginine (R); $X_9$ is selected from the group including leucine (L), lysine (K), arginine (R), glutamine (Q), and histidine (H); $X_{10}$ is selected from the group including lysine (K), phenylalanine (F), alanine (A), cysteine (C), isoleucine (I), valine (V), leucine (L), and methionine (M); and $X_{11}$ is valine (V); and wherein the RNA base-binding motif is operably capable of specifically binding to a cytosine RNA base.

Preferably, the PUF RNA-binding domain of the recombinant polypeptide comprises at least one RNA base-binding motif of the general formula $X_1X_2X_3X_4X_5X_6X_7X_8X_9X_{10}X_{11}$ wherein $X_1$ is glutamine (Q); $X_2$ is tyrosine (Y); $X_3$ is glycine (G); $X_4$ is selected from the group including glycine (G), alanine (A), serine (S), threonine (T) and cysteine (C); $X_5$ is tyrosine (Y); $X_6$ is valine (V); $X_7$ is isoleucine (I); $X_8$ is arginine (R); $X_9$ is histidine (H); $X_{10}$ is valine (V); and $X_{11}$ is leucine (L).

In a more preferred embodiment, the PUF RNA-binding domain of the recombinant polypeptide comprises at least one RNA base-binding motif of the general formula $X_1X_2X_3X_4X_5X_6X_7X_8X_9X_{10}X_{11}$ wherein $X_1$ is glutamine (Q); $X_2$ is tyrosine (Y); $X_3$ is glycine (G); $X_4$ is glycine (G); $X_5$ is tyrosine (Y); $X_6$ is valine (V); $X_7$ is isoleucine (I); $X_8$ is arginine (R); $X_9$ is histidine (H); $X_{10}$ is valine (V); and $X_{11}$ is leucine (L).

In a more preferred embodiment, the PUF RNA-binding domain of the recombinant polypeptide comprises at least one RNA base-binding motif of the general formula $X_1X_2X_3X_4X_5X_6X_7X_8X_9X_{10}X_{11}$ wherein $X_1$ is glutamine (Q); $X_2$ is tyrosine (Y); $X_3$ is glycine (G); $X_4$ is alanine (A); $X_5$ is tyrosine (Y); $X_6$ is valine (V); $X_7$ is isoleucine (I); $X_8$ is arginine (R); $X_9$ is histidine (H); $X_{10}$ is valine (V); and $X_{11}$ is leucine (L).

In a more preferred embodiment, the PUF RNA-binding domain of the recombinant polypeptide comprises at least one RNA base-binding motif of the general formula $X_1X_2X_3X_4X_5X_6X_7X_8X_9X_{10}X_{11}$ wherein $X_1$ is glutamine (Q); $X_2$ is tyrosine (Y); $X_3$ is glycine (G); $X_4$ is serine (S); $X_5$ is tyrosine (Y); $X_6$ is valine (V); $X_7$ is isoleucine (I); $X_8$ is arginine (R); $X_9$ is histidine (H); $X_{10}$ is valine (V); and $X_{11}$ is leucine (L).

In a more preferred embodiment, the PUF RNA-binding domain of the recombinant polypeptide comprises at least one RNA base-binding motif of the general formula $X_1X_2X_3X_4X_5X_6X_7X_8X_9X_{10}X_{11}$ wherein $X_1$ is glutamine (Q); $X_2$ is tyrosine (Y); $X_3$ is glycine (G); $X_4$ is threonine (T); $X_5$ is tyrosine (Y); $X_6$ is valine (V); $X_7$ is isoleucine (I); $X_8$ is arginine (R); $X_9$ is histidine (H); $X_{10}$ is valine (V); and $X_{11}$ is leucine (L).

In a more preferred embodiment, the PUF RNA-binding domain of the recombinant polypeptide comprises at least one RNA base-binding motif of the general formula $X_1X_2X_3X_4X_5X_6X_7X_8X_9X_{10}X_{11}$ wherein $X_1$ is glutamine (Q); $X_2$ is tyrosine (Y); $X_3$ is glycine (G); $X_4$ is cysteine (C); $X_5$ is tyrosine (Y); $X_6$ is valine (V); $X_7$ is isoleucine (I); $X_8$ is arginine (R); $X_9$ is histidine (H); $X_{10}$ is valine (V); and $X_{11}$ is leucine (L).

The PUF RNA-binding domain may comprise at least one RNA base-binding motif of the general formula QYGXYVIRHVL wherein X is an amino acid with a small or nucleophilic side chain; and for the PUF RNA-binding domain to comprise at least one RNA base-binding motif of the general formula QYGXYVIRHVL wherein X is an amino acid selected from the group comprising glycine (G), alanine (A), serine (S), threonine (T), and cysteine (C).

The cytosine may be provided in the form of a target RNA sequence in a target RNA molecule; the target RNA molecule may be any one of messenger RNA (mRNA), transfer RNA (tRNA), ribosomal RNA (rRNA), non-coding RNA, and RNA interference molecules such as short interfering RNA (sRNA) and micro RNA (miRNA).

The term "capable of specifically binding to a cytosine RNA base" as used herein refers to the ability of the PUF RNA-binding domain of the present invention to selectively recognize, interact with, and bind a cytosine RNA base relative to an adenosine, guanine, or uracil RNA base.

The PUF RNA-binding domain may comprise a plurality of RNA base-binding motifs, at least one of which is capable of specifically binding to a cytosine RNA base; and further for the plurality of RNA base-binding motifs to comprise a first RNA base-binding motif capable of specifically binding to a cytosine RNA base and a second RNA base-binding motif capable of specifically binding to an RNA base comprising one of adenosine, guanine, or uracil, wherein the first and second RNA base-binding motifs are synergistically operable to specifically bind the RNA bases.

Typically, the PUF RNA-binding domain comprises a plurality of consecutively ordered RNA base-binding motifs synergistically operable to bind a target RNA molecule with a target RNA sequence, each RNA base-binding motif capable of specifically binding to a cytosine, adenosine, guanine, or uracil RNA base, wherein the consecutive order of the RNA base-binding motifs corresponds with the consecutive order of the RNA bases in the target RNA sequence.

The target RNA molecule may be mRNA encoding a reporter protein including, but not limited to his3, β-galatosidase, GFP, RFP, YFP, luciferase, β-glucuronidase, and alkaline phosphatase.

Preferably, the plurality of consecutively ordered RNA base-binding motifs comprises at least one first RNA base-binding motif having a sequence of any one of SEQ ID NOS: 1-5 and at least one second RNA base-binding motif having a sequence of any one of SEQ ID NOS: 6-13.

The plurality of RNA base-binding motifs may comprise between 2 and 40 RNA base-binding motifs. Preferably, the plurality of RNA base-binding motifs to comprise between 8 and 16 RNA base-binding motifs.

The PUF RNA-binding domain may comprise a plurality of RNA base-binding motifs operably linked via amino acid spacers; for such amino acid spacers to include such as those typically used by persons skilled in the art; and further for the amino acid spacers to be derived, wholly or in part, from any one of human PUM1 (AF315592), Human PUM2 (AF315591), mouse Pum1 (AF321909), Mouse Pum 2 (AF315590), *Xenopus* XPum1 (AAL14121) and *Xenopus* XPum2 (BAB20864) *Trypanosoma* Puf1, Ce Puf-7 (B0273.2), Sc Puf6p (YDR496c), Ce Puf-11 (Y73B6BL.10), Sc Puf1p (JSN1), Sc Puf2p (YPR042C), Ce FBF-2, Ce FBF-1, Ce Puf-3 (Y45F10A.2), Ce Puf-4 (M4.2), Ce Puf-5 (F54C9.8), Ce Puf-6 (F18A11.1), Ce Puf-10 (Y48G1BL.3), Sc Puf5p (MPT5), Dictyost. PufA, DrPum, Anapheles Pum, XPum1, Pum1, PUM1, zfPum1, XPum2, Pum2, PUM2, zfPum2, Ce Puf-8 (C30G12.7), Ce Puf-9 (W06B11.2), AraF14P13.4, AraQ9ZW07, AraF16P2.43, AraF16P2.48, AraAT4g25880, AraF14M19.160, Sc Puf3p (YII013C), *Plasmodium* Pum, Sc Puf4p (YGL023), AraF14D7.5, AraT15F16.9, zebrafish zfPum1 (BQ133093) and zebrafish zfPum2 (AI558582).

The fusion protein of the invention may comprise at least one PUF RNA-binding domain capable of specifically binding to a cytosine RNA base, and an effector domain.

The effector domain of the fusion protein on the invention may be any domain capable of interacting with RNA, whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP S1, Y14, DEK, REF2, and SRm160); proteins and protein domains responsible for stabilizing RNA (for example PABP); proteins and protein domains responsible for repressing translation (for example Agog and Ago4); proteins and protein domains responsible for stimulating translation (for example Staufen); proteins and protein domains responsible for polyadenylation of RNA (for example PAP1, GLD-2, and Star-PAP); proteins and protein domains responsible for polyuridinylation of RNA (for example CID1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription.

The PUF RNA-binding domain of the fusion protein of the invention may comprise at least one RNA base-binding motif of the general formula $X_1X_2X_3X_4X_5X_6X_7X_8X_9X_{10}X_{11}$ wherein $X_1$ is selected from the group including glutamine (Q), valine (V), methionine (M), proline (P), glutamic acid (E), and lysine (K);

$X_2$ is selected from the group including histidine (H), phenylalanine (F), tyrosine (Y), and asparagine (N);

$X_3$ is selected from the group including glycine (G) and alanine (A);

$X_4$ is selected from the group including glycine (G), alanine (A), serine (S), threonine (T) and cysteine (C);

$X_5$ is selected from the group including arginine (R), tyrosine (Y), histidine (H), and asparagine (N);

$X_6$ is selected from the group including phenylalanine (F), leucine (L), and valine (V);

$X_7$ is selected from the group including isoleucine (I), leucine (L), and valine (V);

$X_8$ is arginine (R);

$X_9$ is selected from the group including leucine (L), lysine (K), arginine (R), glutamine (Q), and histidine (H);

$X_{10}$ is selected from the group including lysine (K), phenylalanine (F), alanine (A), cysteine (C), isoleucine (I), valine (V), leucine (L), and methionine (M); and $X_{11}$ is selected from the group including leucine (L), phenylalanine (F), isoleucine (I), and valine (V);

and wherein the RNA base-binding motif is operably capable of specifically binding to a cytosine RNA base.

The PUF RNA-binding domain of the fusion protein of the invention may comprise at least one RNA base-binding motif of the general formula QYGXYVIRHVL wherein X is an amino acid with a small or nucleophilic side chain; and for the PUF RNA-binding domain to comprise at least one RNA base-binding motif of the general formula QYGXYVIRHVL wherein X is an amino acid selected from the group comprising glycine (G), alanine (A), serine (S), threonine (T), and cysteine (C).

The cytosine to which the PUF RNA-binding domain of the fusion protein of the invention is operably capable of specifically binding may be provided in the form of a target RNA sequence in a target RNA molecule; the target RNA molecule may be any one of messenger RNA (mRNA), transfer RNA (tRNA), ribosomal RNA (rRNA), non-coding RNA, and RNA interference molecules such as short interfering RNA (sRNA) and micro RNA (miRNA).

The PUF RNA-binding domain of the fusion protein of the invention may comprise a plurality of RNA base-binding motifs, at least one of which is capable of specifically binding to a cytosine RNA base; and further for the plurality of RNA base-binding motifs to comprise a first RNA base-binding motif capable of specifically binding to a cytosine RNA base and a second RNA base-binding motif capable of specifically binding to an RNA base comprising one of adenosine, guanine, or uracil, wherein the first and second RNA base-binding motifs are synergistically operable to specifically bind the RNA bases.

Preferably, the PUF RNA-binding domain of the fusion protein of the invention comprises a plurality of consecutively ordered RNA base-binding motifs synergistically operable to bind a target RNA molecule with a target RNA sequence, each RNA base-binding motif capable of specifically binding to a cytosine, adenosine, guanine, or uracil RNA base, wherein the consecutive order of the RNA base-binding motifs corresponds with the consecutive order of the RNA bases in the target RNA sequence.

The target RNA molecule to which the fusion protein of the invention is capable of binding may be mRNA encoding a reporter protein including, but not limited to his3, β-galactosidase, GFP, RFP, YFP, luciferase, β-glucuronidase, and alkaline phosphatase.

Preferably, the plurality of consecutively ordered RNA base-binding motifs comprises at least one first RNA base-binding motif having a sequence of any one of SEQ ID NOS: 1-5 and at least one second RNA base-binding motif having a sequence of any one of SEQ ID NOS: 6-13.

Yet further features provide for the PUF RNA-binding domain to comprise a plurality of RNA base-binding motifs operably linked via amino acid spacers; for such amino acid spacers to include such as those typically used by persons skilled in the art; and further for the amino acid spacers to be derived, wholly or in part, from any one of human PUM1 (AF315592), Human PUM2 (AF315591), mouse Pum1 (AF321909), Mouse Pum 2 (AF315590), *Xenopus* XPum1 (AAL14121) and *Xenopus* XPum2 (BAB20864) *Trypanosoma* Puf1, Ce Puf-7 (B0273.2), Sc Puf6p (YDR496c), Ce Puf-11 (Y73B6BL.10), Sc Puf1p (JSN1), Sc Puf2p (YPRO42C), Ce FBF-2, Ce FBF-1, Ce Puf-3 (Y45F10A.2), Ce Puf-4 (M4.2), Ce Puf-5 (F54C9.8), Ce Puf-6 (F18A11.1), Ce Puf-10 (Y48G1BL.3), Sc Puf5p (MPT5), Dictyost. PufA, DrPum, Anapheles Pum, XPum1, Pum1, PUM1, zfPum1, XPum2, Pum2, PUM2, zfPum2, Ce Puf-8 (C30G12.7), Ce Puf-9 (W06B11.2), AraF14P13.4, AraQ9ZW07, AraF16P2.43, AraF16P2.48, AraAT4g25880, AraF14M19.160, Sc Puf3p (YII013C), *Plasmodium* Pum, Sc Puf4p (YGL023), AraF14D7.5, AraT15F16.9, zebrafish zfPum1 (BQ133093) and zebrafish zfPum2 (AI558582).

The PUF RNA-binding domain and the effector domain of the fusion protein of the invention may be operably linked via a peptide spacer.

Due to the degeneracy of the DNA code, it will be well understood to one of ordinary skill in the art that substitution of nucleotides may be made without changing the amino acid sequence of the polypeptide. Therefore, the invention includes any nucleic acid sequence for a recombinant polypeptide comprising a PUF RNA-binding domain capable of specifically binding to a cytosine RNA base. Moreover, it is understood in the art that for a given protein's amino acid sequence, substitution of certain amino acids in the sequence can be made without significant effect on the function of the peptide. Such substitutions are known in the art as "conservative substitutions." The invention encompasses a recombinant polypeptide comprising a PUF RNA-binding domain that contains conservative substitutions, wherein the function of the recombinant polypeptide in the specific binding of a cytosine RNA base is not altered. Generally, the identity of such a mutant recombinant polypeptide comprising a PUF RNA-binding domain will be at least 40% identical to any one of SEQ ID NOS 1-5. More preferably, the mutant recombinant polypeptide comprising a PUF RNA-binding domain will be at least 45%; at least 50%; at least 55%; at least 60%; at least 65%; at least 70%; at least 75%; at least 80%; at least 85%; at least 90%; at least 95%; or at least 97% identical; to any one of SEQ ID NOS 1-5. Most preferably, the mutant recombinant polypeptide comprising a PUF RNA-binding domain will be at least 99% identical to any one of SEQ ID NOS 1-5.

The invention further provides for an isolated nucleic acid encoding the recombinant polypeptide or the fusion protein of the invention.

The isolated nucleic acid of the invention may have a sequence of any one of SEQ ID NOS: 19-23 or any one of SEQ ID NOS: 31-37 or SEQ ID NO: 40.

The isolated nucleic acid encoding the recombinant polypeptide or the fusion protein of the invention may be at least 40% identical; at least 45%; at least 50%; at least 55%; at least 60%; at least 65%; at least 70%; at least 75%; at least 80%; at least 85%; at least 90%; at least 95%; or at least 97% identical; to of any one of SEQ ID NOS: 19-23 or any one of SEQ ID NOS: 31-37 or SEQ ID NO: 40. Most preferably, the isolated nucleic acid encoding the recombinant polypeptide or the fusion protein is at least 99% identical to of any one of SEQ ID NOS: 19-23 or any one of SEQ ID NOS: 31-37 or SEQ ID NO: 40.

The isolated nucleic acid may have a sequence selected from the group comprising any one of SEQ ID NOS: 19-23, any one of SEQ ID NOS: 31-37, or SEQ ID NO: 40, and a sequence at least 80% homologous to any one of SEQ ID NOS: 19-23 and 31-37 or SEQ ID NO: 40.

The recombinant vector of the invention may comprise nucleic acid encoding the recombinant polypeptide or the fusion protein of the invention.

The nucleic acid of the recombinant vector may have a sequence of any one of SEQ ID NOS: 19-23 or any one of SEQ ID NOS: 31-37 or SEQ ID NO: 40. The invention encompasses a recombinant vector comprising nucleic acid encoding the recombinant polypeptide or the fusion protein of the invention that is at least 40% identical to of any one of SEQ ID NOS: 19-23 or any one of SEQ ID NOS: 31-37 or SEQ ID NO: 40. Preferably, the nucleic acid of the recombinant vector will be at least 45%; at least 50%; at least 55%; at least 60%; at least 65%; at least 70%; at least 75%; at least 80%; at least 85%; at least 90%; at least 95%; or at least 97% identical; to of any one of SEQ ID NOS: 19-23 or any one of SEQ ID NOS: 31-37 or SEQ ID NO: 40. Most preferably, the nucleic acid of the recombinant vector will be at least 99% identical to any of any one of SEQ ID NOS: 19-23 or any one of SEQ ID NOS: 31-37 or SEQ ID NO: 40.

The host cells of the invention may comprise nucleic acid encoding the recombinant polypeptide or the fusion protein of the invention, that is at least 40%; at least 45%; at least 50%; at least 55%; at least 60%; at least 65%; at least 70%; at least 75%; at least 80%; at least 85%; at least 90%; at least 95%; or at least 97% identical to any one of SEQ ID NOS: 19-23 or any one of SEQ ID NOS: 31-37 or SEQ ID NO: 40. Most preferably, the nucleic acid of the host cell will be at least 99% identical to any one of SEQ ID NOS: 19-23 or any one of SEQ ID NOS: 31-37 or SEQ ID NO: 40.

Any suitable host cell may be used, including prokaryotic and eukaryotic cells and may be selected according to the chosen expression system such as bacterial, yeast, insect or mammalian expression systems. Regulating sequences for gene expression in the various expression systems may be selected accordingly. Typically, the host cell of the invention is a yeast, preferably *Saccharomyces cerevisiae* YBZ-1.

The recombinant polypeptide of the invention or the fusion protein of the invention may further comprise an operable signal sequence such as those known in the art, including but not limited to a nuclear localization signal (NLS), a mitochondrial targeting sequence (MTS) and a secretion signal. The isolated nucleic acid of the invention, the nucleic acid of the recombinant vector of the invention, and the nucleic acid of the host cell of the invention may encode an operable signal sequence such as those known in the art, including but not limited to a nuclear localization signal (NLS), a mitochondrial targeting sequence (MTS) and a secretion signal. The recombinant polypeptide of the invention or the fusion protein of the invention may further comprise a protein tag such as those known in the art, including but not limited to an intein tag, a maltose binding protein domain tag, a histidine tag, a FLAG-tag, a biotin tag, a strepavidin tag, a starch binding protein domain tag, a hemagglutinin tag, and a fluorescent protein tag.

The polypeptides and proteins of the present invention may be modified peptides, i.e. peptides, which may contain amino acids modified by addition of any chemical residue, such as phosphorylated or myristylated amino acids.

The pharmaceutical composition of the invention comprising the recombinant polypeptide of the invention or the fusion protein of the invention or the isolated nucleic acid of the invention or the recombinant vector of the invention.

The term "pharmaceutical composition" as used herein comprises the substances of the present invention and optionally one or more pharmaceutically acceptable carriers. The substances of the present invention may be formulated as pharmaceutically acceptable salts. Acceptable salts comprise acetate, methylester, HCl, sulfate, chloride and the like. The pharmaceutical compositions can be conveniently administered by any of the routes conventionally used for drug administration, for instance, orally, topically, parenterally or by inhalation. The substances may be administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier (s) must be "acceptable" in the sense of being compatible with the other ingredients of the formulation and not deleterious to the recipient thereof. The pharmaceutical carrier employed may be, for example, either a solid or liquid. Exemplary of solid carriers are lactose, terra alba, sucrose, talc, gelatine, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. The substance according to the present invention can be administered in various manners to achieve the desired effect. Said substance can be administered either alone or in the formulated as pharmaceutical preparations to the subject being treated either orally, topically, parenterally or by inhalation. Moreover, the substance can be administered in combination with other substances either in a common pharmaceutical composition or as separated pharmaceutical compositions. The diluent is selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. A therapeutically effective dose refers to that amount of the substance according to the invention which ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. The dosage regimen will be determined by the attending physician and other clinical factors; preferably in accordance with any one of the methods described above. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. Specific formulations of the substance according to the invention are prepared in a manner well known in the pharmaceutical art and usually comprise at least one active substance referred to herein above in admixture or otherwise associated with a pharmaceutically acceptable carrier or diluent thereof. For making those formulations the active substance(s) will usually be mixed with a carrier or diluted by a diluent, or enclosed or encapsulated in a capsule, sachet, cachet, paper or other suitable containers or vehicles. A carrier may be solid, semisolid, gel-based or liquid material, which serves as a vehicle, excipient or medium for the active ingredients. Said suitable carriers comprise those mentioned above and others well known in the art, see, e.g., Remington's Pharmaceutical Sciences, Mack Publishing Company, Easton, Pennsylvania. The formulations can be adapted to the mode of administration comprising the forms of tablets, capsules, suppositories, solutions, suspensions or the like. The dosing recommendations will be indicated in product labeling by allowing the prescriber to anticipate dose adjustments depending on the considered patient group, with information that avoids prescribing the wrong drug to the wrong patients at the wrong dose.

The PUF RNA-binding domain of the system of the invention, and of the kit of the invention, may comprise at least one RNA base-binding motif as described herein.

The PUF RNA-binding domain of the system of the invention, and of the kit of the invention, may comprise a plurality of RNA base-binding motifs operably linked via amino acid spacers; for such amino acid spacers to include such as those typically used by persons skilled in the art; and further for the amino acid spacers to be derived, wholly or in part, from any one of human PUM1 (AF315592), Human PUM2 (AF315591), mouse Pum1 (AF321909), Mouse Pum 2 (AF315590), *Xenopus* XPum1 (AAL14121) and *Xenopus* XPum2 (BAB20864) *Trypanosoma* Puf1, Ce Puf-7 (B0273.2), Sc Puf6p (YDR496c), Ce Puf-11 (Y73B6BL.10), Sc Puf1p (JSN1), Sc Puf2p (YPR042C), Ce FBF-2, Ce FBF-1, Ce Puf-3 (Y45F10A.2), Ce Puf-4 (M4.2), Ce Puf-5 (F54C9.8), Ce Puf-6 (F18A11.1), Ce Puf-10 (Y48G1BL.3), Sc Puf5p (MPT5), Dictyost. PufA, DrPum, Anapheles Pum, XPum1, Pum1, PUM1, zfPum1, XPum2, Pum2, PUM2, zfPum2, Ce Puf-8 (C30G12.7), Ce Puf-9 (W06B11.2), AraF14P13.4, AraQ9ZW07, AraF16P2.43, AraF16P2.48, AraAT4g25880, AraF14M19.160, Sc Puf3p (YII013C), Plasmodium Pum, Sc Puf4p (YGL023), AraF14D7.5, AraT15F16.9, zebrafish zfPum1 (BQ133093) and zebrafish zfPum2 (A1558582).
Specific Briefly, the invention provides recombinant polypeptides derived from human PUM1 comprising a PUF RNA-binding domain with eight RNA base binding motifs or repeats which are each capable of binding to an RNA base. The recombinant polypeptides of the invention include the first 5 RNA base binding motifs or repeats of human PUM1 (SEQ ID NOS: 6-10) and the last two RNA base binding motifs or repeats (SEQ ID NOS: 11-12). RNA base binding motif or repeat 6 was recombinantly engineered to have the general formula QYGXYVIRHVL in which X is an amino acid with a small or nucleophilic side chain, such as glycine (G), alanine (A), serine (S), threonine (T), and cysteine (C). This recombinantly engineered RNA base binding motif or repeat 6 was surprisingly capable of specifically binding to a cytosine RNA base.

While recombinantly engineered RNA base binding motif or repeats have been prepared for specific binding to adenosine, guanine and uracil, no recombinantly engineered RNA base binding motif or repeat has previously been reported to be specifically capable of binding cytosine. It is thus intended that the modular arrangement of a PUF RNA-binding domain be exploited for the inventive design and preparation of recombinant polypeptides of the invention which are capable of binding to a target RNA molecule having any RNA sequence, simply by the appropriate arrangement of the RNA base binding motifs or repeats with respect to one another. While recombinant polypeptides having eight RNA base binding motifs are herein described, it is understood that the scope of the invention is not limited to the use of any specific number of repeats.

It is further intended that the recombinant RNA base-binding motifs capable of specifically binding cytosine as described herein be combined with other known RNA base-binding motifs capable of specifically binding to adenosine, guanine or uracil. Such a combination is expected to function synergistically to facilitate the specific binding of a PUF RNA-binding domain having an engineered consecutive order of RNA binding motifs to a target RNA molecule, the target RNA sequence of which corresponds with the engineered consecutive order of RNA binding motifs in the recombinant polypeptide. The preparation of such a recombinant polypeptide can be carried out by using recombinant methods known to those skilled in the art.

Effector domains may also be fused to the recombinant polypeptides using recombinant methods known to those skilled in the art to produce fusion proteins. The effector domain may be any domain capable of interacting with RNA, whether transiently or irreversibly, to effect events including but not limited to mRNA processing and transport, translation initiation or inhibition, and mRNA degradation.

It will be appreciated that the cytosine to which the recombinant polypeptide of the invention specifically binds may be present as part of a target RNA sequence in a target RNA molecule and that this RNA is not limited to that of messenger RNA (mRNA) but may be any one of transfer RNA (tRNA), ribosomal RNA (rRNA), non-coding RNA, and RNA interference molecules such as short interfering RNA (sRNA) and micro RNA (miRNA). Furthermore, the target RNA molecule may be an mRNA encoding a reporter protein such as his3, β-galatosidase, GFP, RFP, YFP, luciferase, β-glucuronidase, and alkaline phosphatase, where the invention is used as a research tool. The target RNA molecule may also be an endogenous mRNA transcript where the invention is used as a therapeutic agent. Such endogenous mRNA transcripts are understood to include those produced by infectious agents such as viruses and intracellular pathogens.

Reporter proteins may also be fused to the recombinant polypeptide where the invention is used as a research tool. Examples include his3, β-galatosidase, GFP, RFP, YFP, luciferase, β-glucuronidase, and alkaline phosphatase. Similarly, various tags for facilitating purification proteins of the invention and/or signal sequences such as a nuclear localization signals (NLSs), a mitochondrial targeting sequence (MTS) and secretion signals may be fused thereto, using recombinant methods known to those skilled in the art. Examples include intein tag, a maltose binding protein domain tag, a histidine tag, a FLAG-tag, a biotin tag, a strepavidin tag, a starch binding protein domain tag, a hemagglutinin tag, and a fluorescent protein tag. The amino acid sequence or peptide spacers between the RNA-base binding motifs may be derived from any PUF domain containing protein provided the resultant recombinant polypeptides are capable of operably binding RNA bases as described herein.

The recombinant polypeptides, fusion proteins, isolated nucleic acids, and recombinant vectors of the invention may be used as research tools, in the form of compositions as described herein, or as pharmaceutical compositions if combined with a pharmaceutically acceptable carrier or excipient such as those known in the art.

The invention is further intended to be used to regulate the expression of a specific gene, and to this end methods, systems, and kits are herein provided for the modular preparation of isolated nucleic acid encoding RNA base-binding motifs in a desired consecutive order which is capable of specifically binding cytosine, adenosine, guanine or uracil in the order in which they are included in a corresponding RNA target molecule. Once such nucleic acid has been recombinantly prepared, it may be inserted into a recombinant vector, such as pGAD-RC, using methods known in the art, and introduced into a cell and expressed. The effect on gene expression may be monitored using techniques known in the art, including but not limited to yeast three-hybrid growth assays using the his3 reporter gene system, and β-galactosidase assays.

EXAMPLE 1

Introduction

Figure 2:
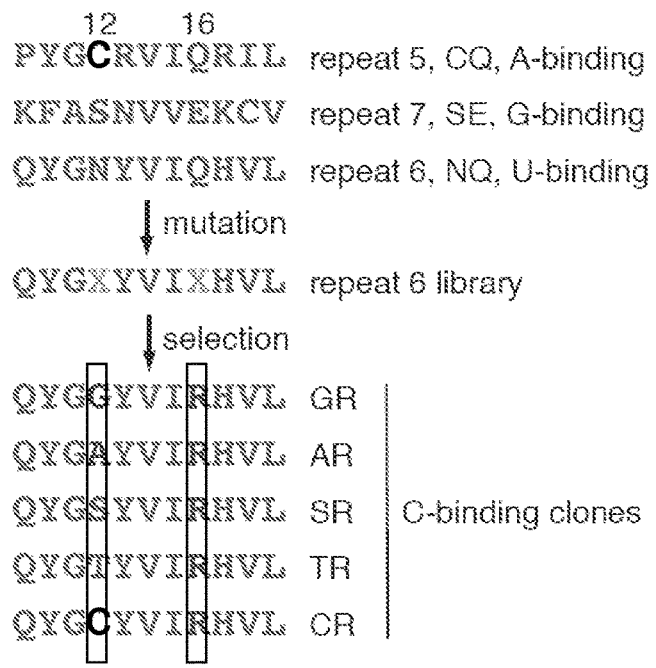
FIG. 2 is a diagrammatic representation and alignment of the amino acid sequences comprising recombinant PUF domain repeat 6 of embodiments of the invention, as compared with PUF domain repeats 5 and 7. The sequences from top to bottom are SEQ ID NO: 10, SEQ ID NO: 12, SEQ ID NO: 11, SEQ ID NO: 62, SEQ ID NO: 1, SEQ ID NO: 2, SEQ ID NO: 3, SEQ ID NO: 4, and SEQ ID NO: 5. The recombinant PUF domain repeat 6 of the preferred embodiments of the invention has amino acids with small or nucleophilic side chains such as glycine (GR), alanine (AR), serine (SR), threonine (TR) and cysteine (CR) at position 12 (left box) together with arginine at position 16 (right box). The residues at positions 12 and 16 were randomised and combinations that could recognize cytosine were selected fro m the library using the yeast three-hybrid system.

Referring to FIGS. 1 and 2, PUF (*Drosophila Pumilio* and *Caenorhabitis elegans* FBF homology) domains are typically composed of eight 36 amino acid repeats repeat binding to a single nucleotide in its extended RNA target via hydrogen bonding or van der Waals contacts between amino acids at positions 12 and 16 and the Watson-Crick edge. The amino acid at position 13 makes a stacking interaction.

Although PUF domains with repeats that recognize adenine, guanine or uracil have been reported (Cheong, C. G. & Hall, T. M. (2006) PNAS 103: 13635-13639; Wang, X./ et al (2002) Cell 110: 501-512), the use of these PUF domains has been substantially hampered by the lack of residues known to specifically recognise cytosine.

Materials and Methods

Plasmids

To produce a Gal4p activation domain fused to a PUF domain, a synthetic gene encoding amino acids 828 to 1176 of the human PUM1 protein (GenBank accession no. NP_001018494, GENEART) was subcloned into pGAD-RC (pGAD-RC: Ito, T. et al (2000) 97: 1143-1147). This plasmid was used as a template for library construction by enzymatic inverse PCR (enzymatic inverse PCR: Rackham, O. & Chin, J. W. (2005) Nat Chem Biol 1: 159-166) using primers where the codons corresponding to amino acids 1043 and 1047 were encoded by mixtures of trimer phosphoramidites encoding all 20 amino acids (GeneWorks). Individual Puf domain mutants were also made by enzymatic inverse PCR. RNA expression plasmids were made by altering the multiple cloning site of pIIIA/MS2-2 (pIIIA/MS2-2: Stumpf, C. R. et al (2008) Methods Enzymol 449: 295-315) according to the method of Cassiday and Maher (Cassiday, L. A. & Maher, L. J. (2001) Biochemistry 40: 2433-2438) and subcloning pairs of annealed oligonucleotides corresponding to the following RNA sequences (PUF recognition sequences in bold, site specific mutations underlined):

```
NRE:
                                    (SEQ ID NO: 42)
5'-CCGGCUAGCAAUUGUAUAUAUUAAUUUAAUAAAGCAUG-3';

NREU3A:
                                    (SEQ ID NO: 43)
5'-CCGGCUAGCAAUUGAAUAUAUUAAUUUAAUAAAGCAUG-3';

NREU3C:
                                    (SEQ ID NO: 44)
5'-CCGGCUAGCAAUUGCAUAUAUUAAUUUAAUAAAGCAUG-3';

NREU3G:
                                    (SEQ ID NO: 45)
5'-CCGGCUAGCAAUUGGAUAUAUUAAUUUAAUAAAGCAUG-3'.
```

PUF Library Selections

Saccharomyces cerevisiae YBZ-1 cells (MATa, ura3-52, leu2-3, 112, his3-200, trp 1-1, ade2, LYS2 :: (LexAop)-HIS3, ura3 :: (lexA-op)-lacZ, LexA-MS2 coat (N55K)) (Hook, B. et al. (2005) RNA 11: 227-233) containing the NREU3C RNA expression plasmid were transformed with the PUF domain library in pGAD-RC using the LiAc method according to the method of Gietz and Woods (Gietz, R. D. & Woods, R. A. (2002) Methods Enzymol 350: 87-96) yielding $6 \times 10^5$ primary transformants. Cells were amplified by overnight growth in SC media lacking leucine and uracil, washed in TE and $1 \times 10^7$ CFU were plated on SC agar lacking leucine, uracil and histidine, supplemented with 0.5 mM 3-amino triazole. Colonies were picked after three days and the plasmids were isolated, transformed into Escherichia coli DH10B, screened by PCR to identify the PUF encoding plasmid which was sequenced and transformed into YBZ-1 to analyze the specificity of the mutant PUF domains, as described below.

Yeast Three-Hybrid Growth Assays

YBZ-1 transformants containing PUF domain and RNA expression plasmids were grown overnight in SC media lacking leucine and uracil, washed in SC media without amino acids, diluted to $OD_{600}$ of 0.1 and replica spotted onto SC media lacking leucine and uracil (to test for cell health and plasmid maintenance) and SC agar lacking leucine, uracil and histidine, supplemented with 0.5 mM 3-amino triazole (to test for RNA-protein interactions).

β-Galactosidase Assays

YBZ-1 transformants containing PUF domain and RNA expression plasmids were grown overnight in SC media lacking leucine and uracil, diluted to $OD_{600}$ of 0.1 and mixed with an equal volume of Beta-Glo reagent (Promega), incubated for 1 h at room temperature and luminescence was detected using a FLUOstar OPTIMA (BMB Labtech).

Purification of PUF Proteins

PUF domains were subcloned into pTYB3 and expressed as a fusion to an intein and chitin-binding domain in Escherichia coli ER2566 cells (New England Biolabs). Cells were lyzed by sonication in 20 mM sodium phosphate (pH 8.0), 1 M NaCl, and 0.1 mM PMSF. Lysates were clarified by centrifugation and incubated for 40 min with chitin beads (New England Biolabs). Beads were washed twice with 20 mM sodium phosphate (pH 8.0), 1 M NaCl, and 0.1 mM PMSF, once with 20 mM sodium phosphate (pH 8.0), 0.5 M NaCl, and 0.1 mM PMSF, and once with 20 mM sodium phosphate (pH 8.0), 0.15 M NaCl, and 0.1 mM PMSF. DTT was added to the beads to 50 mM final concentration and the tube was purged with nitrogen gas before incubation at room temperature with gentle rocking for three days. Cleaved PUF domain protein, free from the intein and chitin-binding domain was collected, transferred into 10 mM Tris-HCl (pH 7.4), 150 mM NaCl, 5 mM β-mercaptoethanol and further purified by an ÄKTA-Explorer system (GE) using a Superdex 200 10/300 column (GE) with a total bed volume of 120 ml. Pure fractions were pooled and concentrated using Microsep 10K Omega centrifugal devices (PALL). Protein concentration was determined by the bicichroninic acid (BCA) assay using bovine serum albumin (BSA) as a standard.

RNA Electrophoretic Mobility Shift Assays

Purified PUF domains were incubated at room temperature for 30 min with fluorescein labeled RNA oligonucleotides (Dharmacon) in 10 mM HEPES (pH 8.0), 1 mM EDTA, 50 mM KCl, 2 mM DTT, 0.1 mg/ml fatty acid-free BSA, and 0.02% Tween-20. The following RNA sequences were used:

```
NRE:      5'-(Fl)AUUGUAUAUA-3'; (SEQ ID NO: 46)

NREU3C:   5'-(Fl)AUUGCAUAUA-3'. (SEQ ID NO: 47)
```

Reactions were analyzed by 10% PAGE in TAE and fluorescence was detected using a Typhoon TRIO scanner (GE).

Results

Figure 3:
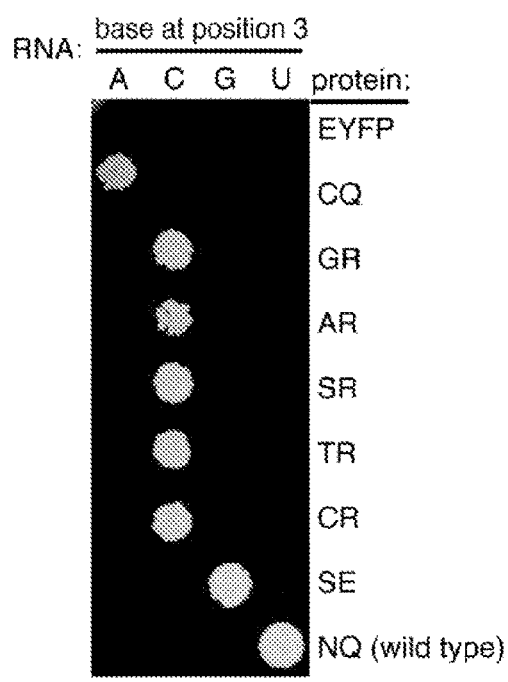
FIG. 3 is a photograph of a plate yeast three-hybrid growth assay of selected *Saccharomyces cerevisiae* YBZ-1 transformants variously co-expressing the recombinant proteins of the invention and RNA expression plasmids. Growth of the selected clones on selective SC media lacking leucine, uracil, and histidine, supplemented with 0.5 mM 3-amino triazole was indicative of his3 reporter gene activation and therefore specific RNA-recombinant protein interaction.
Figure 4:
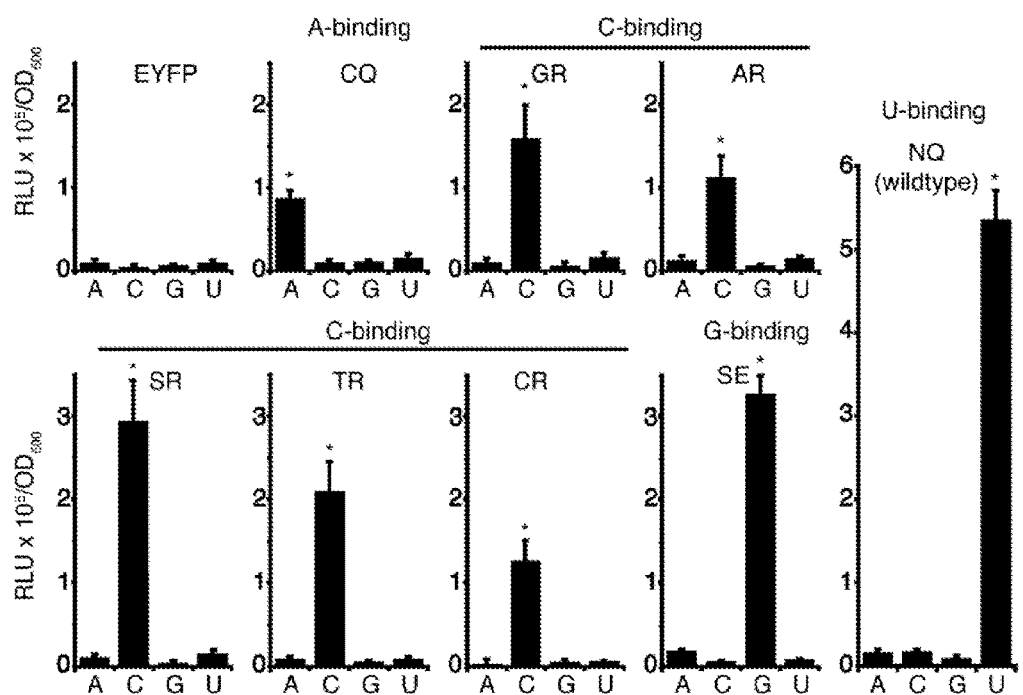
FIG. 4 is a series of bar graphs showing of selected *Saccharomyces cerevisiae* YBZ-1 transformants variously co-expressing the recombinant proteins of the invention and RNA expression plasmids. The ratio of luminescence to cell density ($RLU \times 10^5/OD_{600}$) was plotted against the identity of the base at position 3 of the target RNA sequence as quantified using β-galactosidase assays for the detection of lacZ reporter gene activation. Increased luminescence was indicative of specific RNA-recombinant protein interaction.

The eight repeats of the PUF domain of human PUM1 recognise only the adenine, guanine and uracil RNA bases of NRE RNA (FIG. 1). To address the need for a PUF domain capable of specifically recognising cytosine, a library of human PUM1 PUF domains was synthesized in which positions 12 and 16 of repeat six were randomized so as to encode all possible amino acids. The recombinant PUM1 PUF domain proteins were combined with an RNA target in which the corresponding base was altered to cytosine, and specific RNA-protein interactions detected using the yeast three hybrid system (Thomson, E. et al (2007) RNA 13: 2165-2174). Activation of the his3 reporter gene was expected to occur upon specific interaction between the recombinant PUM1 PUF domain proteins and the RNA targets. Five unique mutants were identified that exhibited protein-dependent reporter activation, the repeat 6 amino acid sequence for which is shown in FIG. 2. These protein variants interacted with RNAs containing a cytosine but not adenine, guanine or uracil as determined by growth on selective media and quantified using β-galactosidase assays to examine activation of a lacZ reporter gene (FIGS. 3 and 4). All five protein variants exhibited an asparagine at position 16 and an amino acid with a small or nucleophilic side chain at position 12 (glycine, alanine, serine, threonine, or cysteine).

Figure 5:
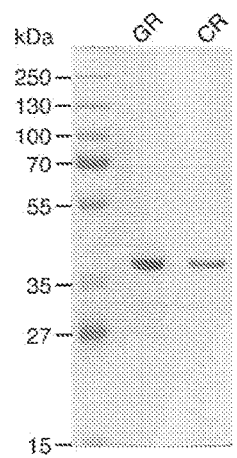
FIG. 5 is a scan of an SDS PAGE gel showing resolved samples of the purified preparations of GR and CR.
Figure 6:
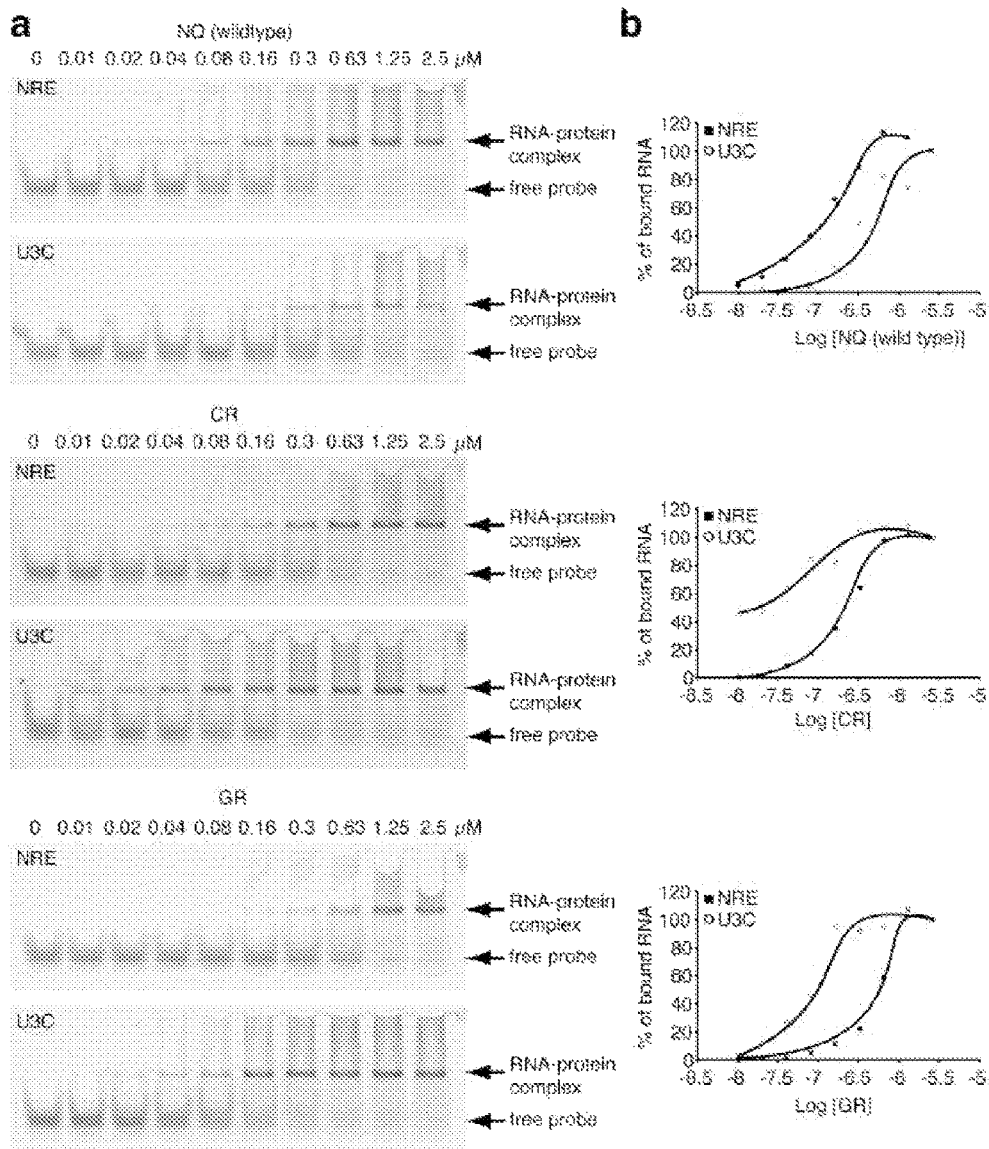
FIG. 6 shows (*a*) scans of 10% polyacrylamide gels on which RNA electrophoretic mobility shift assays using purified NQ (wildtype) (upper panel), CR (middle panel) and GR (lower panel) recombinant proteins and RNA oligonucleotides NRE and U3C were resolved, and (*b*) line graphs in which the percentage of RNA bound by varying concentrations of each protein is shown.

Two of these protein variants (GR, with glycine at position 12 and arginine at position 16, and CR, with cysteine at position 12 and arginine at position 16) were recombinantly expressed in Escherichia coli and purified to homogeneity (FIG. 5). RNA electrophoretic mobility shift assays using these proteins showed a striking specificity shift between the selected PUF domains and a cytosine containing RNA and the wild type PUF and its cognate RNA (FIG. 6). The amino acid sequences of the GR, AR, SR, TR, and CR recombinant proteins of the invention are shown in FIG. 7.

EXAMPLE 2

Materials and Methods
Plasmids

Plasmids expressing individual Puf domain mutants were prepared according to Example 1. RNA expression plasmids were also prepared according to Example 1, except that pairs of annealed oligonucleotides corresponding to the following RNA sequences were used (PUF recognition sequences in bold, site specific mutations underlined):

```
                                      (SEQ ID NO: 42)
NRE:
5'-CCGGCUAGCAAUUGUAUAUAUUAAUUUAAUAAAGCAUG-3';

(SEQ ID NO: 48)
NREU1C:
5'-CCGGCUAGCAAUCGUAUAUAUUAAUUUAAUAAAGCAUG-3';

(SEQ ID NO: 49)
NREG2C:
5'-CCGGCUAGCAAUUCUAUAUAUUAAUUUAAUAAAGCAUG-3';

(SEQ ID NO: 44)
NREU3C:
5'-CCGGCUAGCAAUUGCAUAUAUUAAUUUAAUAAAGCAUG-3';

(SEQ ID NO: 50)
NREA4C:
5'-CCGGCUAGCAAUUGUCUAUAUUAAUUUAAUAAAGCAUG-3';

(SEQ ID NO: 51)
NREU5C:
5'-CCGGCUAGCAAUUGUACAUAUUAAUUUAAUAAAGCAUG-3';

(SEQ ID NO: 52)
NREA6C:
5'-CCGGCUAGCAAUUGUAUCUAUUAAUUUAAUAAAGCAUG-3';

(SEQ ID NO: 53)
NREU7C:
5'-CCGGCUAGCAAUUGUAUACAUUAAUUUAAUAAAGCAUG-3';

(SEQ ID NO: 54)
NREA8C:
5'-CCGGCUAGCAAUUGUAUAUCUUAAUUUAAUAAAGCAUG-3';

(SEQ ID NO: 55)
NREstem5:
5'-CCGGCUAGCAAUUGUAUAUAUUAAUAUAAUAAAGCAUG-3';

(SEQ ID NO: 56)
NREstem6:
5'-CCGGCUAGCAAUUGUAUAUAUUAAUAUAUUAAAGCAUG-3';

(SEQ ID NO: 57)
NREstem7:
5'-CCGGCUAGCAAUUGUAUAUAUUAAUAUAUAAAAGCAUG-3';

(SEQ ID NO: 58)
NREstem8:
5'-CCGGCUAGCAAUUGUAUAUAUUAAUAUAUACAAGCAUG-3'.
```

Yeast three-hybrid growth assays and β-galactosidase assays were carried out according to Example 1.

Results

Figure 8:
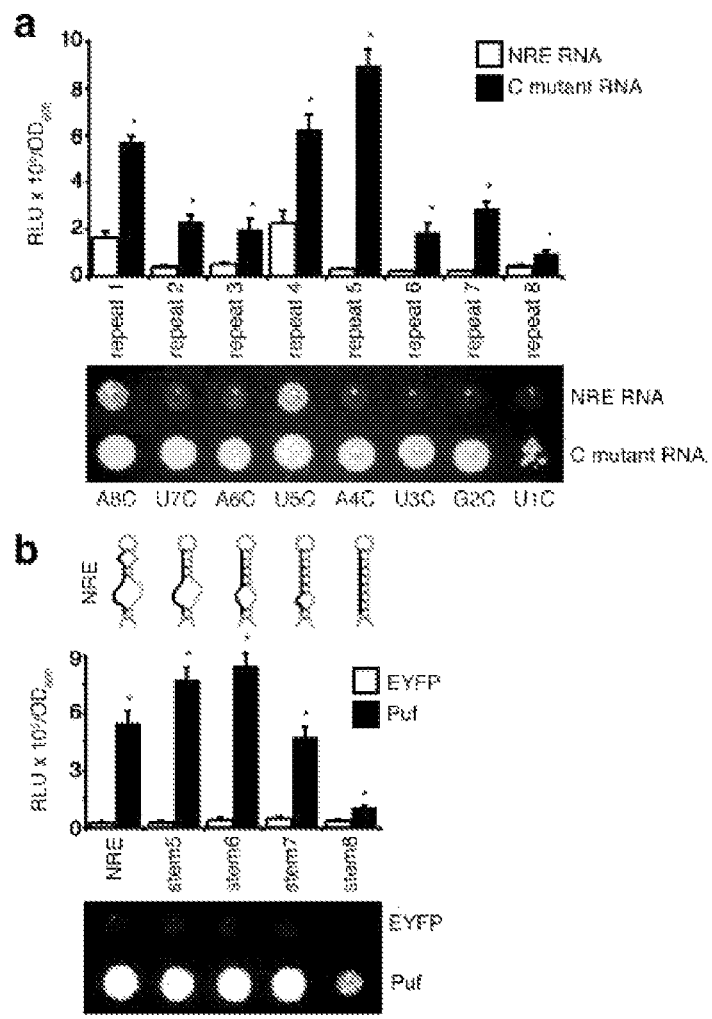
FIG. 8 shows (*a*) a photograph of a plate yeast three-hybrid growth assay (lower panel) of selected *Saccharomyces cerevisiae* YBZ-1 transformants co-expressing recombinant proteins of the invention having engineered PUF repeats in which residues 12 and 16 of the individual repeats were mutated to glycine and arginine respectively, and either the wildtype (NRE) RNA or a mutant NRE where the corresponding base was changed to cytosine. An accompanying bar graph showing corresponding β-galactosidase assays is shown in the upper panel. The engineered PUF repeats were introduced into each of the eight positions of the PUF RNA-base binding domain. Growth of the selected clones on selective SC media lacking leucine, uracil, and histidine, supplemented with 0.5 mM 3-amino triazole was indicative of his3 reporter gene activation and therefore specific RNA-recombinant protein interaction. The engineered PUF domain is able to bind to RNA targets that are located within substantially double stranded RNA structures as shown by (b) a photograph of a plate yeast three-hybrid growth assay of selected *Saccharomyces cerevisiae* YBZ-1 transformants co-expressing recombinant proteins of the invention engineered to target RNA with stem structures, as illustrated by the accompanying bar graph showing corresponding β-galactosidase assays (middle panel) and the diagrammatic representations of the target RNA with stem structures (upper panel).

To determine the general applicability of the selected sequences to design PUF domains for binding to desired RNA sequences, a set of eight PUM1 mutants were prepared wherein repeats 1 to 8 of PUM1 were each altered to have a glycine at position 12 and an arginine at position 16 (GR). These engineered PUF domains were found to specifically bind to an RNA target with cytosine, but not adenine, guanine or uracil, at the position corresponding to the mutated repeat, as assessed by yeast three-hybrid growth assays and β-galactosidase assays (FIG. 8a). All of these engineered PUF domains were found to specifically bind to their engineered RNA target with higher affinity than the wild-type, non-cytosine-containing RNA target.

Furthermore, the PUF domain of human PUM1 was found to bind RNA in which the sequence downstream of the NRE was modified sequentially to place the NRE in increasingly base-paired structures. This PUF domain of human PUM1 was found to be able to bind all the RNA targets (FIG. 8b) including one in which every base was paired in a stem, albeit with less efficiency. This indicates the potential of the recombinant polypeptides of the invention to invade structured RNAs to bind to their target sequences, which is relevant to the rational engineering of these PUF domains.

EXAMPLE 3

Materials and Methods
Plasmids

Plasmids expressing individual Puf domain mutants were prepared according to Example 1, except that to make a 16 repeat Puf protein (PUF×2), repeats 1-8 of the human PUM1 cDNA were amplified using primers that incorporated flanking SacI sites, digested with SacI and cloned into an engineered SacI site that encodes amino acids 1030 and 1031 of the synthetic gene encoding the PUM1 PUF domain. RNA expression plasmids were also prepared according to Example 1, except that pairs of annealed oligonucleotides corresponding to the following RNA sequences were used:

```
NREx2 (SEQ ID NO: 59):
5'-CCGGCUAGCAAUUGUUGUAUAUAAUAUAUUAAUUUAAUAAAGCAU
G-3';

NREx2mut1 (SEQ ID NO: 60):
5'-CCGGCUAGCAAUCCCUGUAUAUAAUAUAUUAAUUUAAUAAAGCAU
G-3';

NREx2mut2 (SEQ ID NO: 61):
5'-CCGGCUAGCAAUUGUCCCCUAUAAUAUAUUAAUUUAAUAAAGCAU
G-3'
```

Yeast three-hybrid growth assays and β-galactosidase assays were carried out according to Example 1.

Results

Figure 9:
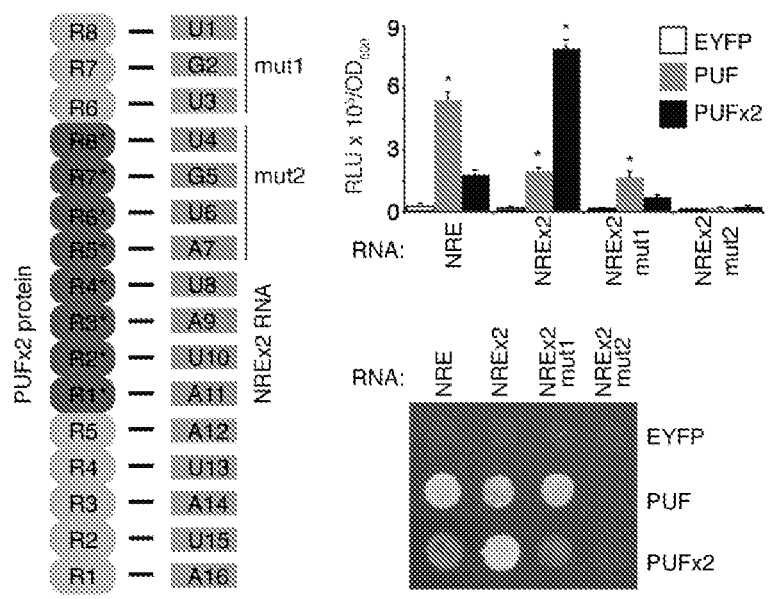
FIG. 9 shows a PUF domain consisting of 16 RNA-binding repeats. The structure of the engineered 16 repeat PUF and its cognate RNA target are shown schematically in the left panel. A photograph of a plate yeast three-hybrid growth assay is shown on the lower panel demonstrating selected *Saccharomyces cerevisiae* YBZ-1 transformant survival on media with 0.5 mM 3-aminotriazole and lacking histidine. A bar graph showing the results of β-galactosidase assays used to determine the interaction of PUF domains and their RNA targets is shown in the upper panel. The NREz×2 mut1 RNA has the UGU triplet of the newly added target region mutated to CCC, and the NRE×2 mutt RNA has the UGU triplet of the native NRE mutated to CCC. The wild type PUF protein is shown to bind just as well to NRE×2 mut1 as it does to NRE×2.

Naturally occurring PUF proteins typically contain eight RNA-binding repeats. Although this is sufficient for them to selectively regulate specific developmental processes, they often do so by binding multiple different RNAs (Gerber, A. P., Herschlag, D. & Brown, P. O. PLoS Biol 2, E79 (2004)). For many applications in biotechnology, synthetic biology and medicine it would be highly desirable to be able to target only one species of RNA within an entire transcriptome. To achieve such levels of sequence discrimination, we engineered PUFs with 16 RNA-binding repeats. We inserted sequences encoding only the RNA-binding PUF repeats, without flanking regions, from the human PUM1 cDNA between repeats five and six of a synthetic gene that encodes the same protein sequence as the PUM1 cDNA but is only 78% similar at the DNA level, to avoid potential instability of the recombinant DNA. Because the *C. elegans* FBF-1 and FBF-2 PUF proteins contain a short insertion close to the end of repeat five, we reasoned that this region might tolerate the insertion of extra PUF repeats. The extended PUF bound to its cognate extended RNA target in yeast and activated transcription of the 3-galactosidase reporter gene more efficiently than the eight repeat PUF with its cognate RNA (FIG. 9, upper panel). The inserted and flanking PUF repeats contributed to the binding affinity and selectivity as separately mutating the UGU triplets recognized by both sets of repeats significantly decreased β-galactosidase activity and growth on selective media (FIG. 9, lower panel). Engineered PUF domain proteins containing 16 RNA-binding repeats provide the means to selectively bind RNAs in higher eukaryotes that have more complex transcriptomes.

Surprisingly, the inventors of this application have successfully engineered a recombinant PUF domain capable of specifically binding cytosine, and not adenine, guanine or uracil, a function of which wild-type PUM1 protein is not capable.

The recombinant polypeptides and fusion proteins of the invention provide alternative agents potentially useful in the specific and targeted regulation of gene expression, and the methods of the invention provide alternative methods of potentially specifically regulating gene expression. The recombinant polypeptides, fusion proteins, and isolated nucleic acids of the invention are not subject to the same design constraints as are RNAi agents. Furthermore, the binding of the recombinant polypeptides and fusion proteins of the invention are sequence-specific and not limited the Watson and Crick base pairing, minimising non-specific binding to non-target RNA molecules and thus off-site effects. In contrast, each PUF repeat typically recognizes a single RNA base through three conserved side chains, two that make hydrogen bond or van der Waals interactions with the edge of an RNA base and a third side chain that stacks with the same base and/or the preceding base.

Further advantages of the use of the recombinant polypeptides and fusion proteins of the invention include the ease with which they may be introduced into cells without the need for using immunogenic transfection reagents or delivery vehicles, increased efficiency of introduction into cells, independence from processing by RNAi machinery, the scope by which the mechanism of gene expression regulation may be carried out by transcript degradation as well as translation inhibition. The fusion proteins of the invention allow for the convenient delivery into cells of a single entity capable of both specific targeting and binding of a target RNA molecule as well as its processing, inhibition, or transport.

The invention claimed is:

1. A recombinant polypeptide comprising at least one PUF RNA-binding domain, wherein the PUF RNA-binding domain comprises at least one RNA base-binding motif having formula $X_1X_2X_3X_4X_5X_6X_7X_8X_9X_{10}X_{11}$ wherein
$X_1$ is glutamine (Q), $X_2$ is histidine (H); $X_3$ is glycine (G); $X_4$ is selected from the group including glycine (G), alanine (A), serine (S), threonine (T) and cysteine (C); $X_5$ is arginine (R); $X_6$ is phenylalanine (F); $X_7$ is isoleucine (I); $X_8$ is arginine (R); $X_9$ is leucine (L); $X_{10}$ is lysine (K); and $X_{11}$ is leucine (L); or $X_1$ is valine (V); $X_2$ is phenylalanine (F); $X_3$ is glycine (G); $X_4$ is selected from the group including glycine (G), alanine (A), serine (S), threonine (T) and cysteine (C); $X_5$ is tyrosine (Y); $X_6$ is valine (V); $X_7$ is isoleucine (I); $X_8$ is arginine (R); $X_9$ is lysine (K); $X_{10}$ is phenylalanine (F); and $X_{11}$ is phenylalanine (F); or $X_1$ is methionine (M); $X_2$ is tyrosine (Y); $X_3$ is glycine (G); $X_4$ is selected from the group including glycine (G), alanine (A), serine (S), threonine (T) and cysteine (C); $X_5$ is arginine (R); $X_6$ is valine (V); $X_7$ is isoleucine (I); $X_8$ is arginine (R); $X_9$ is lysine (K); $X_{10}$ is alanine (A); and $X_{11}$ is leucine (L); or $X_1$ is glutamine (Q); $X_2$ is asparagine (N); $X_3$ is glycine (G); $X_4$ is selected from the group including glycine (G), alanine (A), serine (S), threonine (T) and cysteine (C); $X_5$ is histidine (H); $X_6$ is valine (V); $X_7$ is valine (V); $X_8$ is arginine (R); $X_9$ is lysine (K); $X_{10}$ is cysteine (C); and $X_{11}$ is isoleucine (I); or $X_1$ is proline (P); $X_2$ is tyrosine (Y); $X_3$ is glycine (G); $X_4$ is selected from the group including glycine (G), alanine (A), serine (S), threonine (T) and cysteine (C); $X_5$ is arginine (R); $X_6$ is valine (V); $X_7$ is isoleucine (I); $X_8$ is arginine; (R); $X_9$ is arginine (R); $X_{10}$ is isoleucine (I); and $X_{11}$ is leucine (L); or $X_1$ is glutamine (Q); $X_2$ is tyrosine (Y); $X_3$ is glycine (G); $X_4$ is selected from the group including glycine (G), alanine (A), serine (S), threonine (T) and cysteine (C); $X_5$ is tyrosine (Y); $X_6$ is valine (V); $X_7$ is isoleucine (I); $X_8$ is arginine; (R); $X_9$ is histidine (H); $X_{10}$ is valine (V); and $X_{11}$ is leucine (L); or $X_1$ is lysine (K); $X_2$ is phenylalanine (F); $X_3$ is alanine (A); $X_4$ is selected from the group including glycine (G), alanine (A), serine (S), threonine (T) and cysteine (C); $X_5$ is asparagine (N); $X_6$ is valine (V); $X_7$ is valine (V); $X_8$ is arginine; (R); $X_9$ is lysine (K); $X_{10}$ is cysteine (C); and $X_{11}$ is valine (V); or $X_1$ is glutamine (Q); $X_2$ is tyrosine (Y); $X_3$ is alanine (A); $X_4$ is selected from the group including glycine (G), alanine (A), serine (S), threonine (T) and cysteine (C); $X_5$ is tyrosine (Y); $X_6$ is valine (V); $X_7$ is valine (V); $X_8$ is arginine; (R); $X_9$ is lysine (K); $X_{10}$ is methionine (M); and $X_{11}$ is isoleucine (I).

2. A recombinant polypeptide comprising at least one PUF RNA-binding domain, wherein the PUF RNA-binding domain comprises at least one RNA base-binding motif having formula $X_1X_2X_3X_4X_5X_6X_7X_8X_9X_{10}X_{11}$ wherein $X_1$ is glutamine (Q); $X_2$ is tyrosine (Y); $X_3$ is glycine (G); $X_4$ is selected from the group including glycine (G), alanine (A), serine (S), threonine (T) and cysteine (C); $X_5$ is tyrosine (Y); $X_6$ is valine (V); $X_7$ is isoleucine (I); $X_8$ is arginine (R); $X_9$ is histidine (H); $X_{10}$ is valine (V); and $X_{11}$ is leucine (L).

3. The polypeptide according to claim 1, wherein the PUF RNA-binding domain comprises a plurality of RNA base-binding motifs.

4. The polypeptide according to claim 1, wherein the PUF RNA-binding domain comprises a plurality of consecutively ordered RNA base-binding motifs synergistically operable to bind a target RNA molecule with a target RNA sequence, wherein the consecutive order of the RNA base-binding motifs corresponds with the consecutive order of the RNA bases in the target RNA sequence.

5. The polypeptide according to claim 4, wherein the plurality of consecutively ordered RNA base-binding motifs comprises at least one first RNA base-binding motif having a sequence of any one of SEQ ID NO: 1, SEQ ID NO: 2, SEQ ID NO: 3, SEQ ID NO: 4, SEQ ID NO: 5 and at least one second RNA base-binding motif having a sequence of any one of SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

6. The polypeptide according to claim 4, wherein a plurality of RNA base-binding motifs are operably linked via amino acid spacers.

7. The polypeptide according to claim 6, wherein the amino acid spacers are derived from SEQ ID NO: 39, or part thereof.

8. The polypeptide according to claim 1, wherein the recombinant polypeptide has a sequence of any one of SEQ ID NO: 14, SEQ ID NO: 15, SEQ ID NO: 16, SEQ ID NO: 17, SEQ ID NO: 18; or any one of SEQ ID NO: 24, SEQ ID NO: 25, SEQ ID NO: 26, SEQ ID NO: 27, SEQ ID NO: 28, SEQ ID NO: 29, SEQ ID NO: 30 and SEQ ID NO: 41.

9. A fusion protein comprising at least one PUF RNA-binding domain, and an effector domain wherein the PUF RNA-binding domain comprises at least one RNA base-binding motif having formula $X_1X_2X_3X_4X_5X_6X_7X_8X_9X_{10}X_{11}$ wherein
$X_1$ is glutamine (Q), $X_2$ is histidine (H); $X_3$ is glycine (G); $X_4$ is selected from the group including glycine (G), alanine (A), serine (S), threonine (T) and cysteine (C); $X_5$ is arginine (R); $X_6$ is phenylalanine (F); $X_7$ is isoleucine (I); $X_8$ is arginine (R); $X_9$ is leucine (L); $X_{10}$ is lysine (K); and $X_{11}$ is leucine (L); or $X_1$ is valine (V); $X_2$ is phenylalanine (F); $X_3$ is glycine (G); $X_4$ is selected from the group including glycine (G), alanine (A), serine (S), threonine (T) and cysteine (C); $X_5$ is tyrosine (Y); $X_6$ is valine (V); $X_7$ is isoleucine (I); $X_8$ is arginine (R); $X_9$ is lysine (K); $X_{10}$ is phenylalanine (F); and $X_{11}$ is phenylalanine (F); or $X_1$ is methionine (M); $X_2$ is tyrosine (Y); $X_3$ is glycine (G); $X_4$ is selected from the group including glycine (G), alanine (A), serine (S), threonine (T) and cysteine (C); $X_5$ is arginine (R); $X_6$ is valine (V); $X_7$ is isoleucine (I); $X_8$ is arginine (R); $X_9$ is lysine (K); $X_{10}$ is alanine (A); and $X_{11}$ is leucine (L); or $X_1$ is glutamine (Q); $X_2$ is asparagine (N); $X_3$ is glycine (G); $X_4$ is selected from the group including glycine (G), alanine (A), serine (S), threonine (T) and cysteine (C); $X_5$ is histidine (H); $X_6$ is valine (V); $X_7$ is valine (V); $X_8$ is arginine (R); $X_9$ is lysine (K); $X_{10}$ is cysteine (C); and $X_{11}$ is isoleucine (I); or $X_1$ is proline (P); $X_2$ is tyrosine (Y); $X_3$ is glycine (G); $X_4$ is selected from the group including glycine (G), alanine (A), serine (S), threonine (T) and cysteine (C); $X_5$ is arginine (R); $X_6$ is valine (V); $X_7$ is isoleucine (I); $X_8$ is arginine; (R); $X_9$ is arginine (R); $X_{10}$ is isoleucine (I); and $X_{11}$ is leucine (L); or $X_1$ is glutamine (Q); $X_2$ is tyrosine (Y); $X_3$ is glycine (G); $X_4$ is selected from the group including glycine (G), alanine (A), serine (S), threonine (T) and cysteine (C); $X_5$ is tyrosine (Y); $X_6$ is valine (V); $X_7$ is isoleucine (I); $X_8$ is arginine; (R); $X_9$ is histidine (H); $X_{10}$ is valine (V); and $X_{11}$ is leucine (L); or $X_1$ is lysine (K); $X_2$ is phenylalanine (F); $X_3$ is alanine (A); $X_4$ is selected from the group including glycine (G), alanine (A), serine (S), threonine (T) and cysteine (C); $X_5$ is asparagine (N); $X_6$ is valine (V); $X_7$ is valine (V); $X_8$ is arginine; (R); $X_9$ is lysine (K); $X_{10}$ is cysteine (C); and $X_{11}$ is valine (V); or $X_1$ is glutamine (Q); $X_2$ is tyrosine (Y); $X_3$ is alanine (A); $X_4$ is selected from the group including glycine (G), alanine (A), serine (S), threonine (T) and cysteine (C); $X_5$ is tyrosine (Y); $X_6$ is valine (V); $X_7$ is valine (V); $X_8$ is arginine; (R); $X_9$ is lysine (K); $X_{10}$ is methionine (M); and $X_{11}$ is isoleucine (I).

10. The fusion protein according to claim 9, wherein the effector domain is selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription.

11. A fusion protein comprising at least one PUF RNA-binding domain, an effector domain and at least one polypeptide according to claim 1.

* * * * *